(12) United States Patent
Lee et al.

(10) Patent No.: US 8,167,933 B2
(45) Date of Patent: May 1, 2012

(54) ANNULOPLASTY APPARATUS AND METHODS

(75) Inventors: Andrew Lee, San Jose, CA (US);
Norman Fung, San Francisco, CA (US);
John D. Nguyen, San Jose, CA (US);
Nga T. Doan, San Jose, CA (US);
Laurent Schaller, Los Altos, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/880,823

(22) Filed: Sep. 13, 2010

(65) Prior Publication Data

US 2011/0004298 A1    Jan. 6, 2011

Related U.S. Application Data

(63) Continuation of application No. 10/985,768, filed on Nov. 10, 2004, now abandoned, which is a continuation of application No. 10/125,811, filed on Apr. 18, 2002, now abandoned.

(51) Int. Cl.
*A61F 2/24* (2006.01)

(52) U.S. Cl. ............................. 623/2.11; 623/2.36
(58) Field of Classification Search .......... 623/2.36–2.37
See application file for complete search history.

(56) References Cited

U.S. PATENT DOCUMENTS 6,613,059 B2 * 9/2003 Schaller et al. ............... 606/157

* cited by examiner

*Primary Examiner* — David H. Willse

(57) ABSTRACT

An annuloplasty system for repairing a valve in a patient's heart comprises a surgical implant including a member having first and second end portions. The implant member further is configured and/or adapted to form a partial ring along a portion of one of the valve annulae of a patient's heart such as the mitral or tricuspid valve annulus. The implant member is axially elastic such that it can axially expand and contract and includes first and second anchors extending from the end portions of the implant member. The anchors are adapted to anchor the implant in tissue such as the mitral or tricuspid valve annulus. The system can facilitate tissue plication (e.g., of the posterior annulus of the mitral valve or the annulus of the tricuspid valve) and reinforcement of a valve annulus.

16 Claims, 20 Drawing Sheets

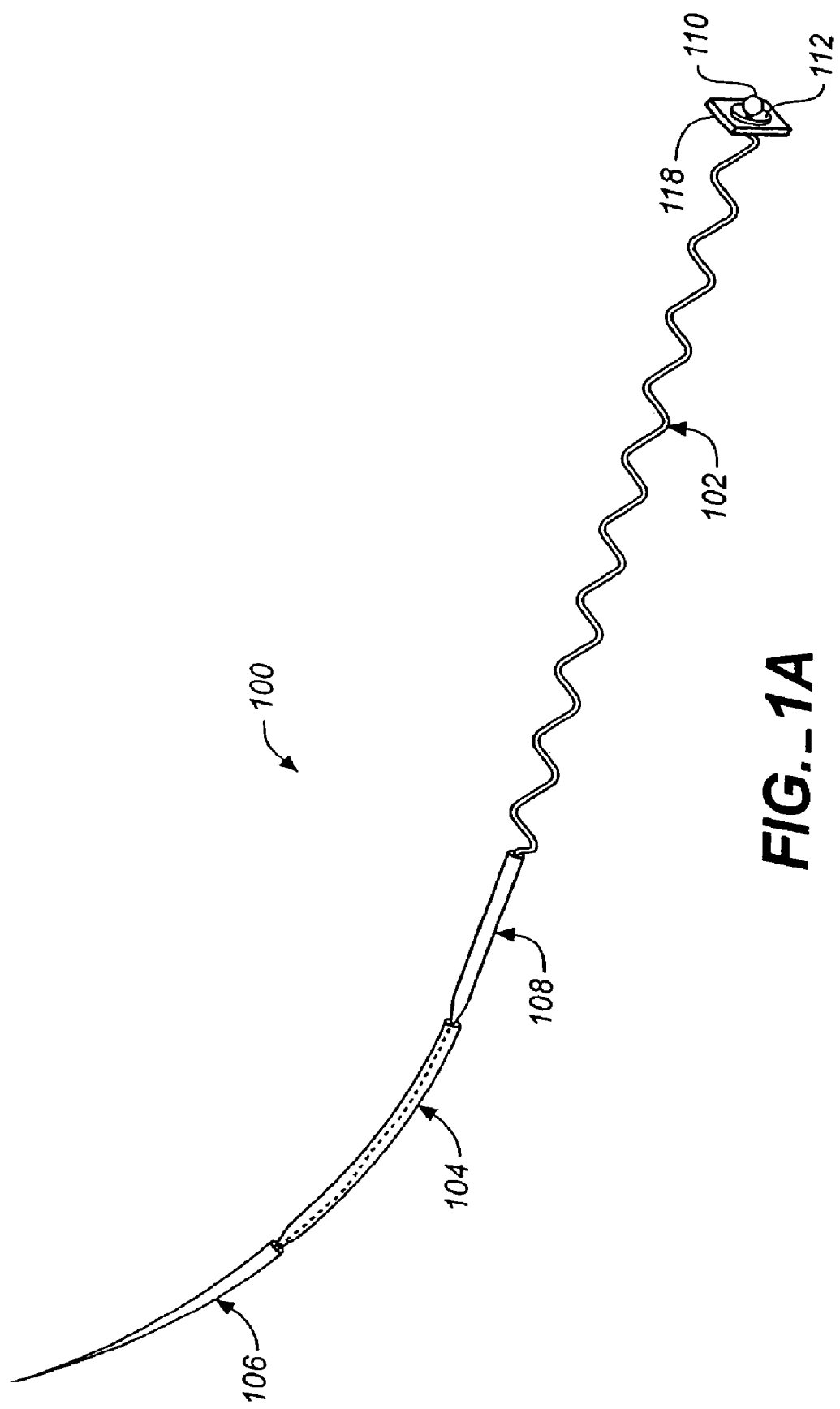

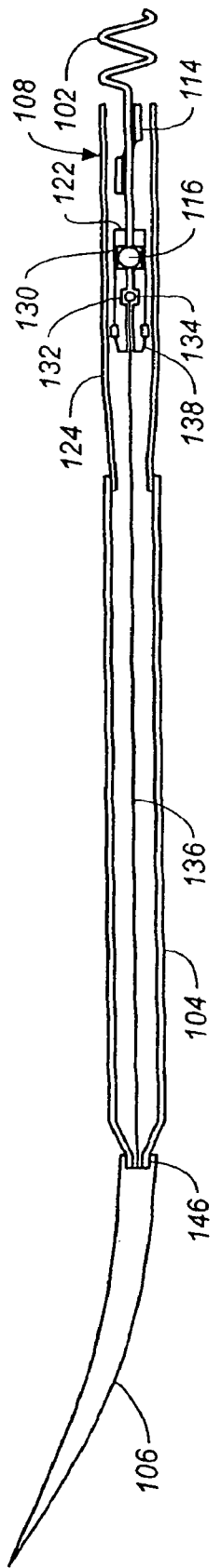
FIG._1B
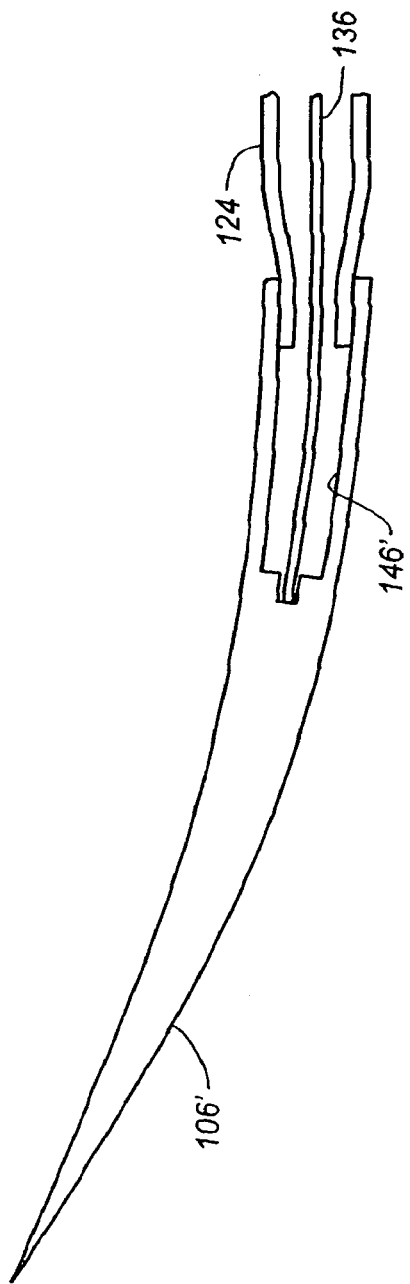
FIG._1C

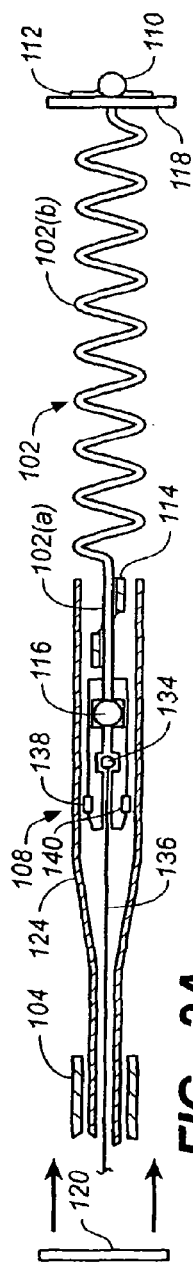
*FIG._2A*
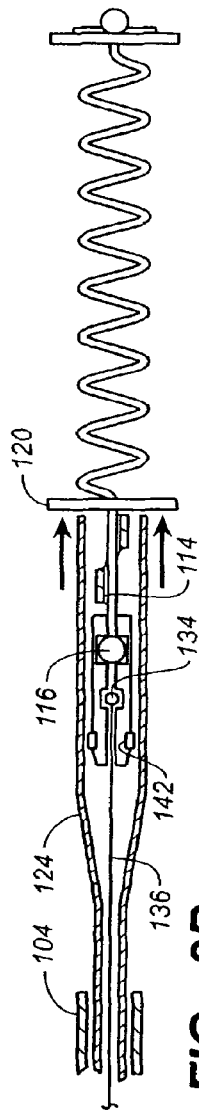
*FIG._2B*
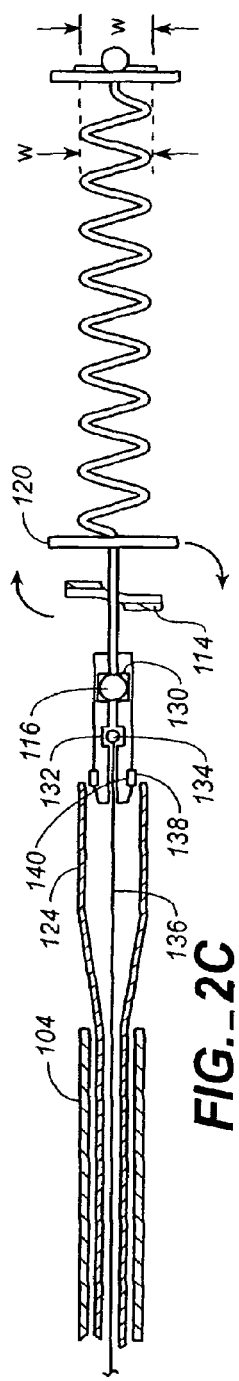
*FIG._2C*
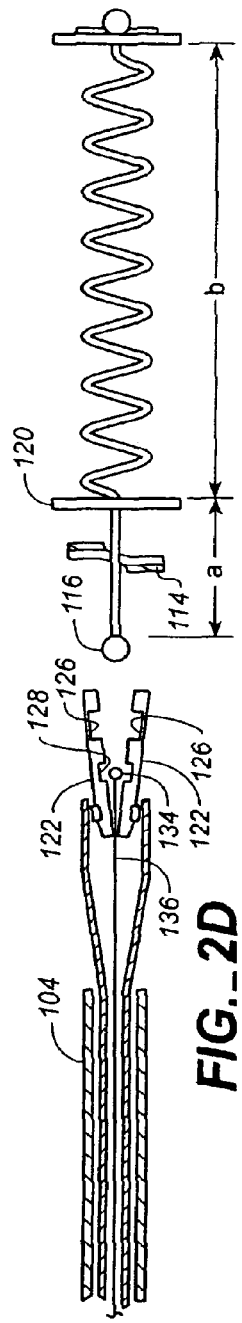
*FIG._2D*

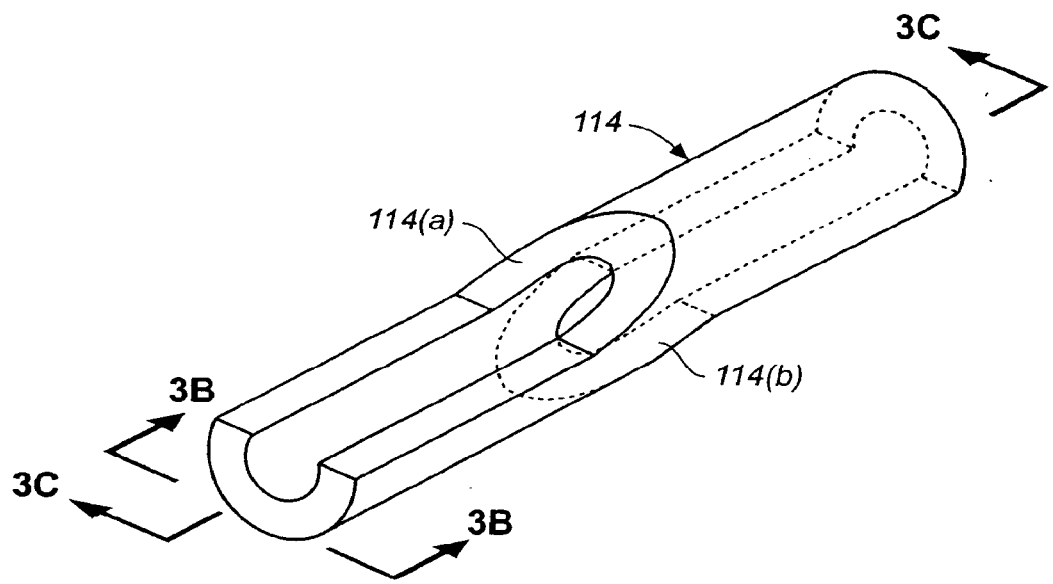
FIG._3A
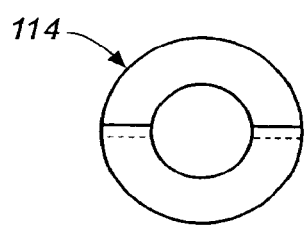
FIG._3B
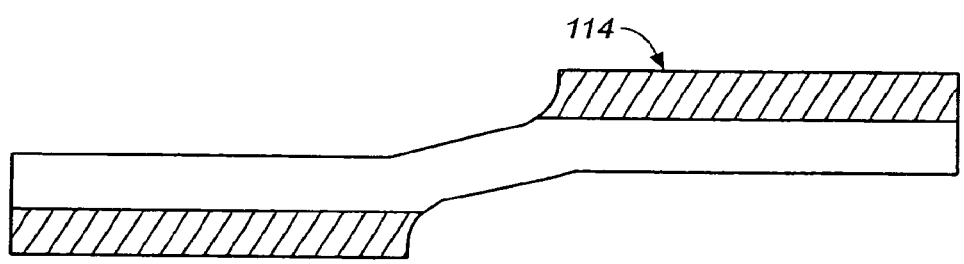
FIG._3C

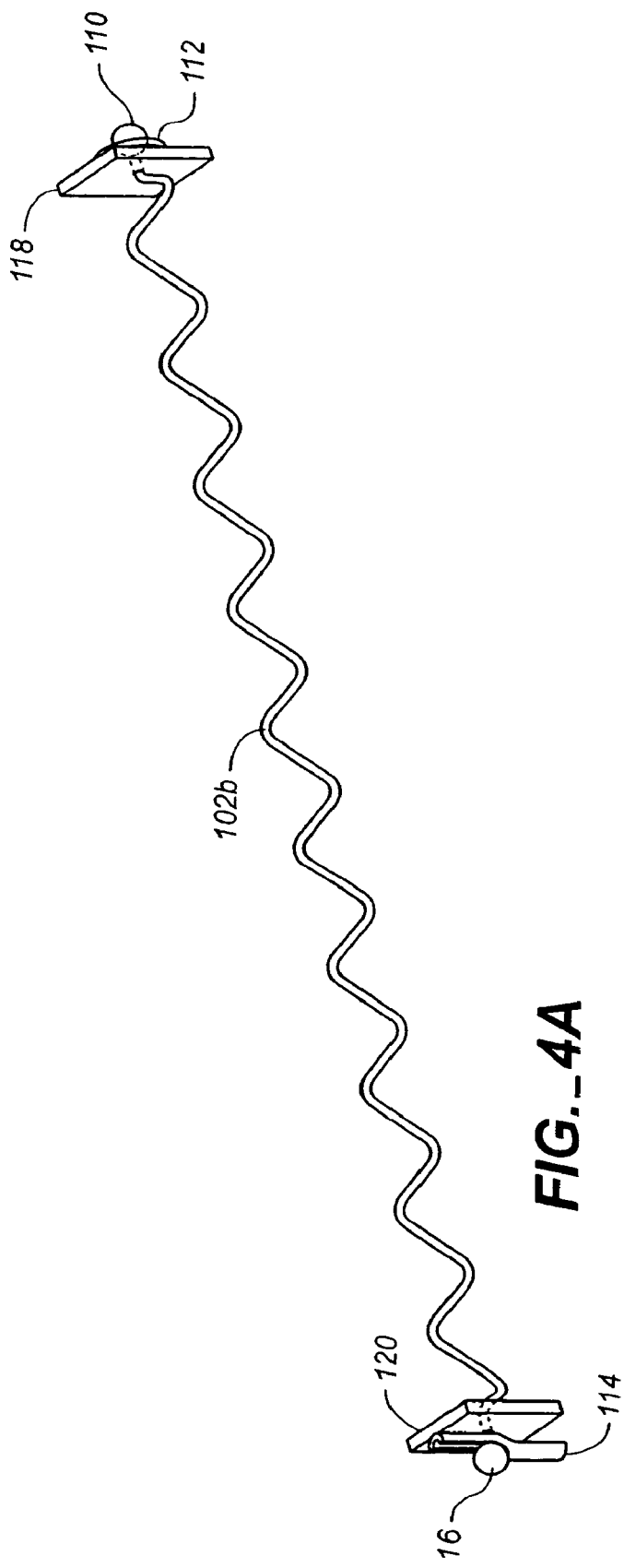
FIG._4A
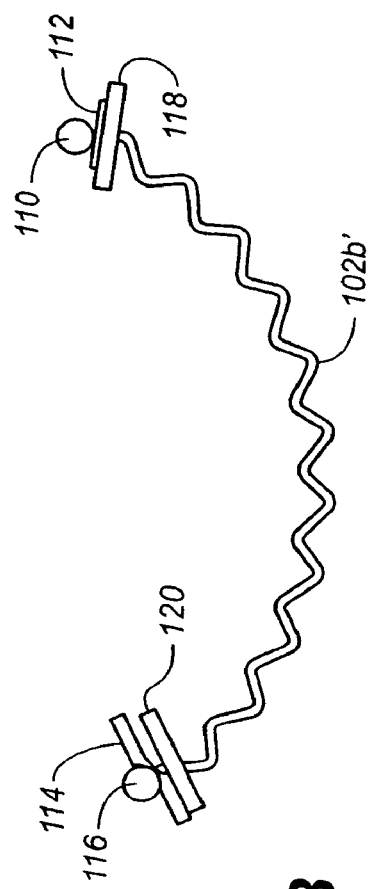
FIG._4B

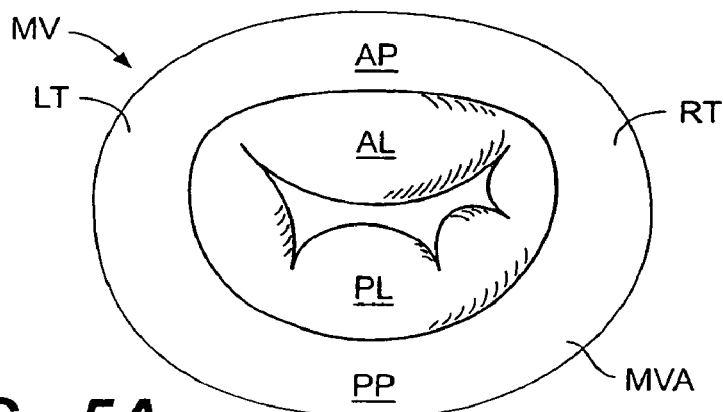
FIG._5A
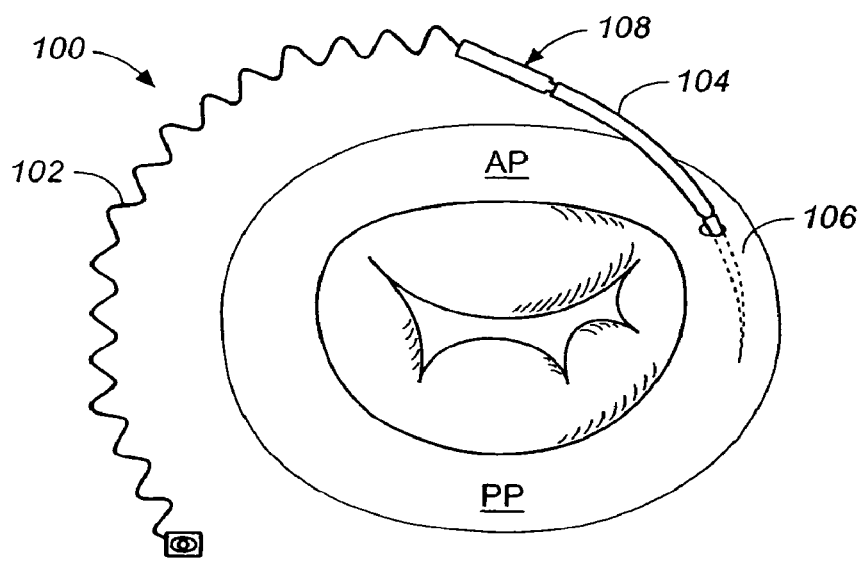
FIG._5B
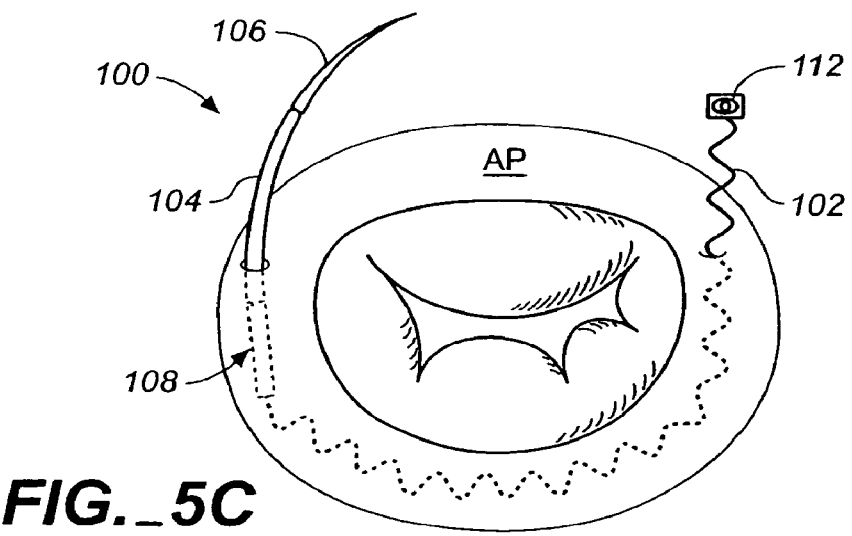
FIG._5C

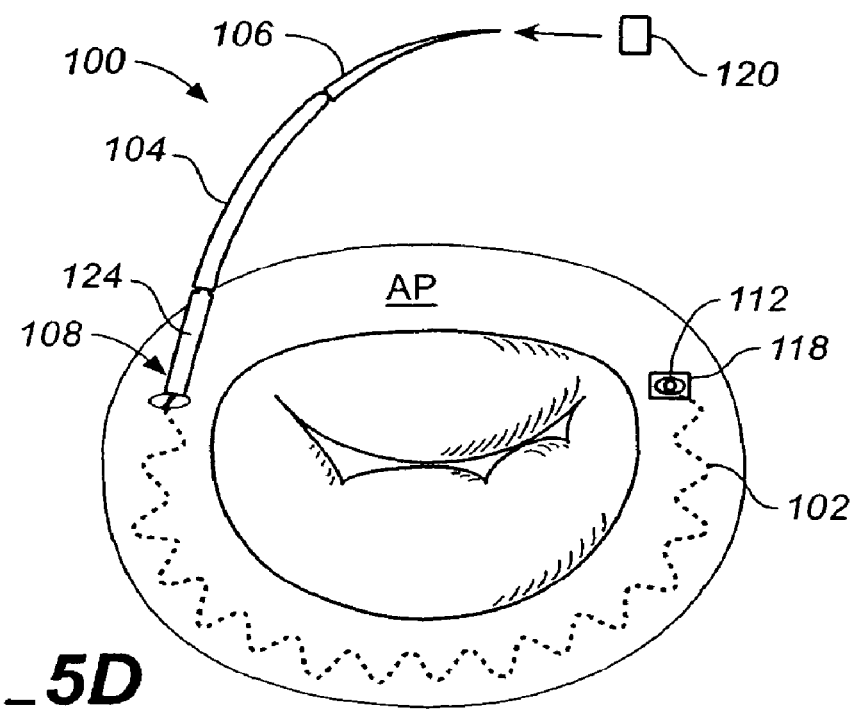
FIG._5D
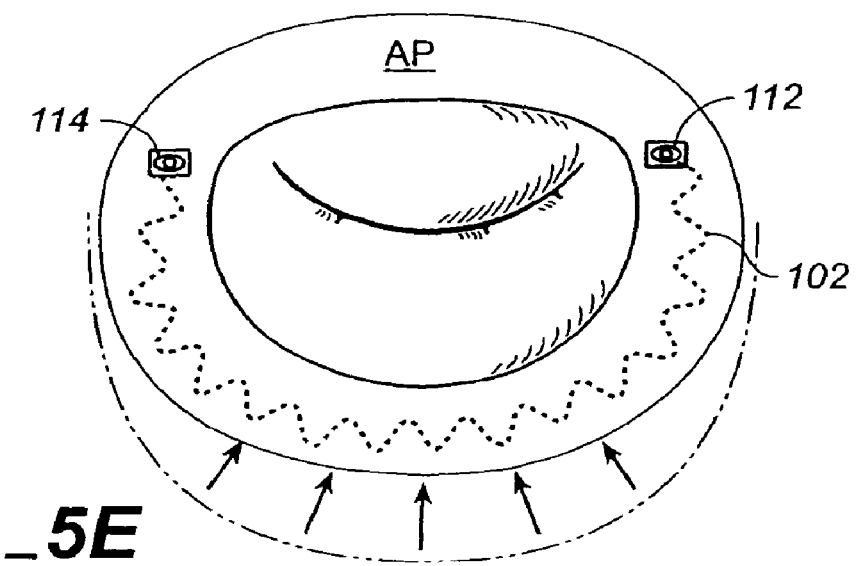
FIG._5E

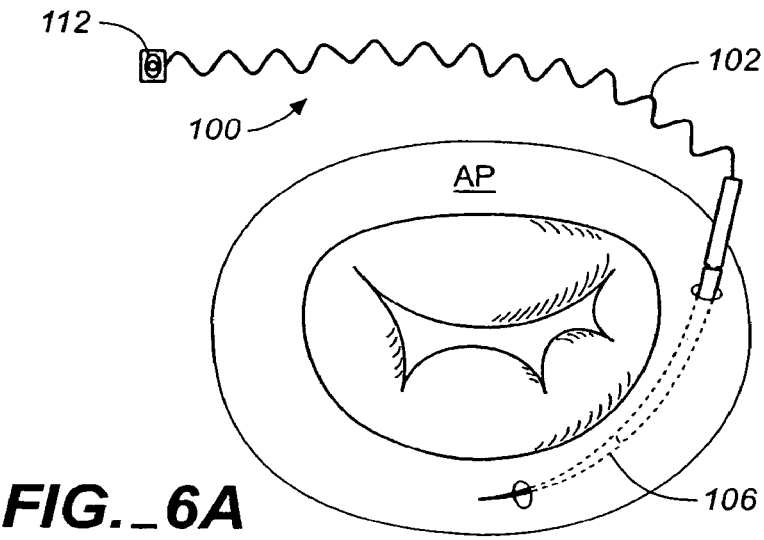
FIG._6A
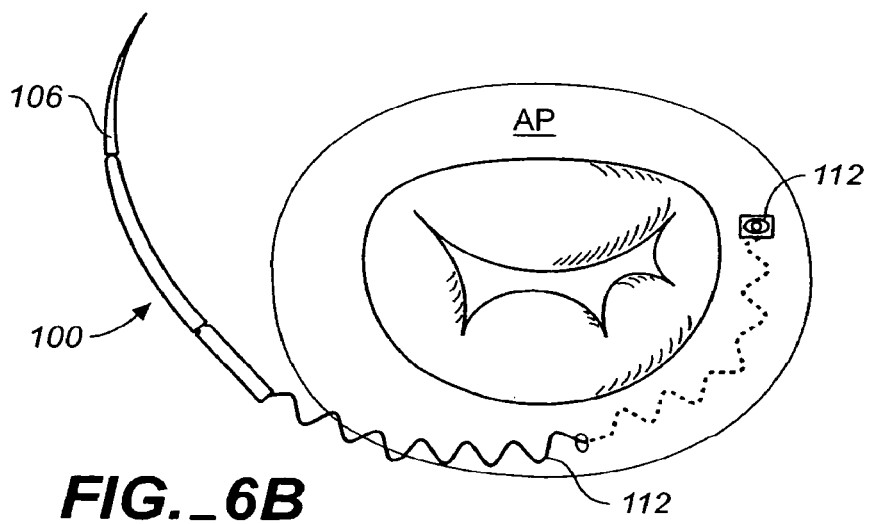
FIG._6B
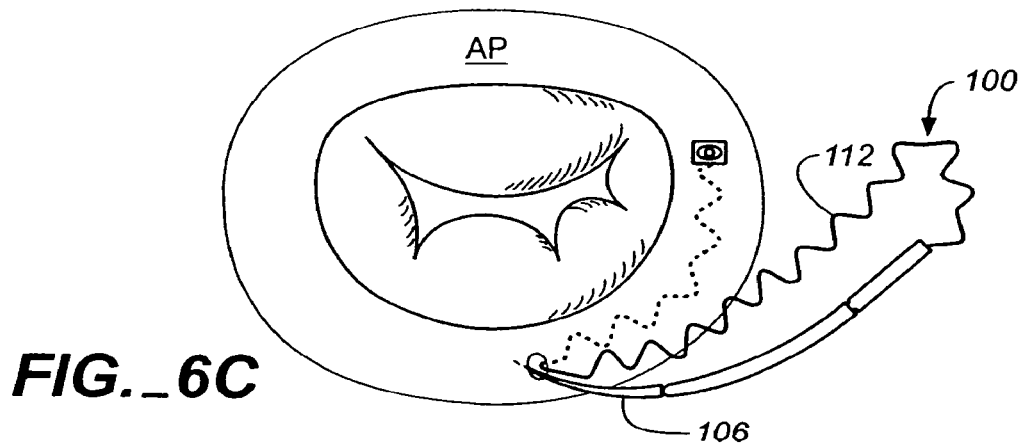
FIG._6C

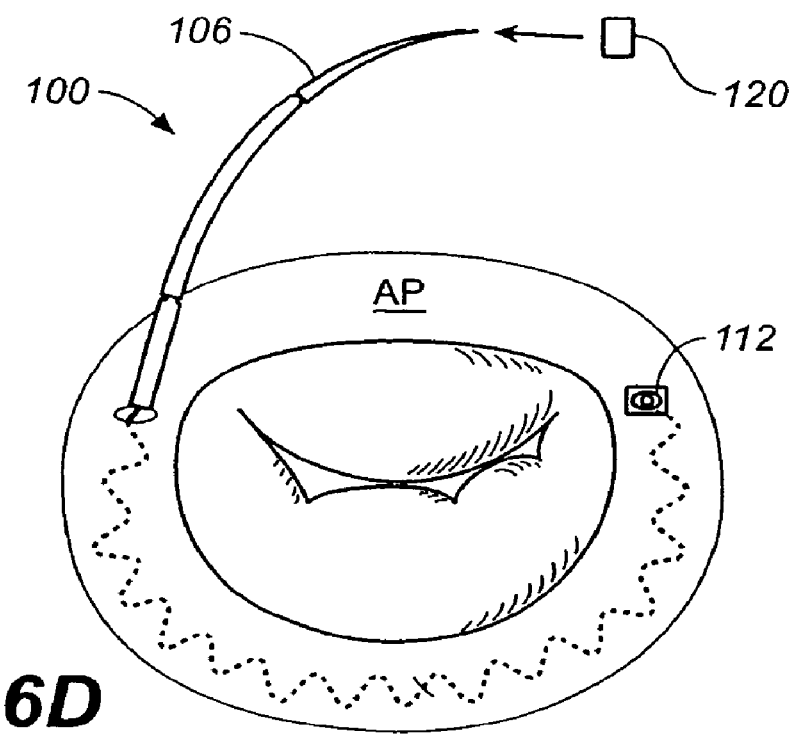
FIG._6D
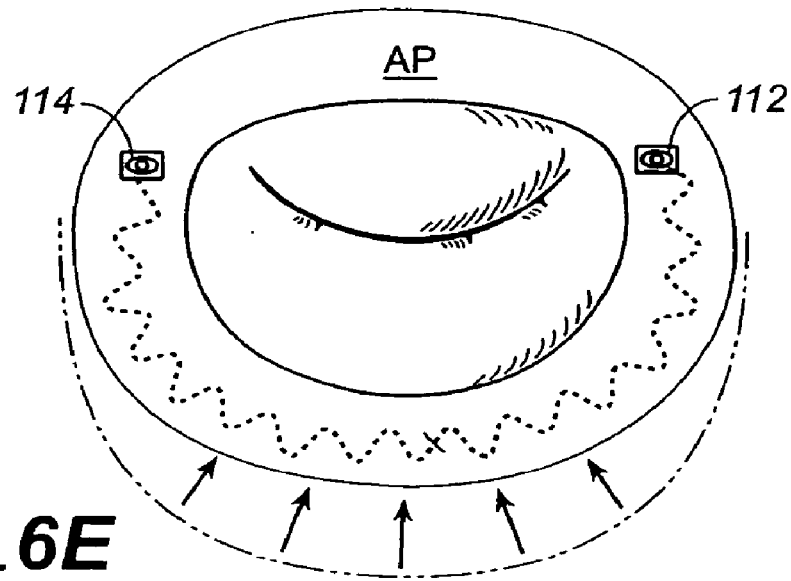
FIG._6E

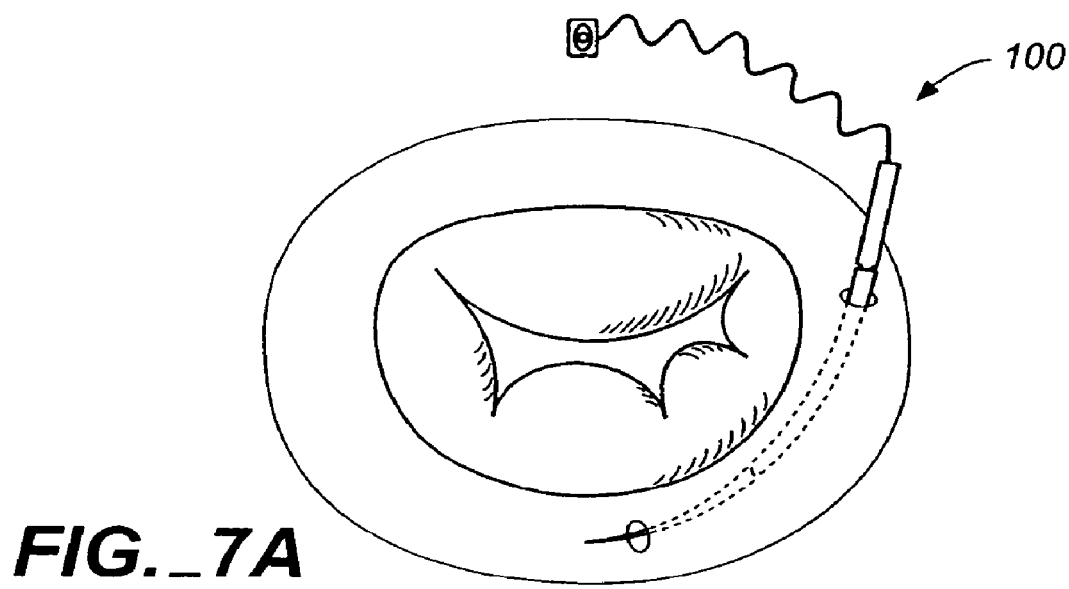
FIG._7A
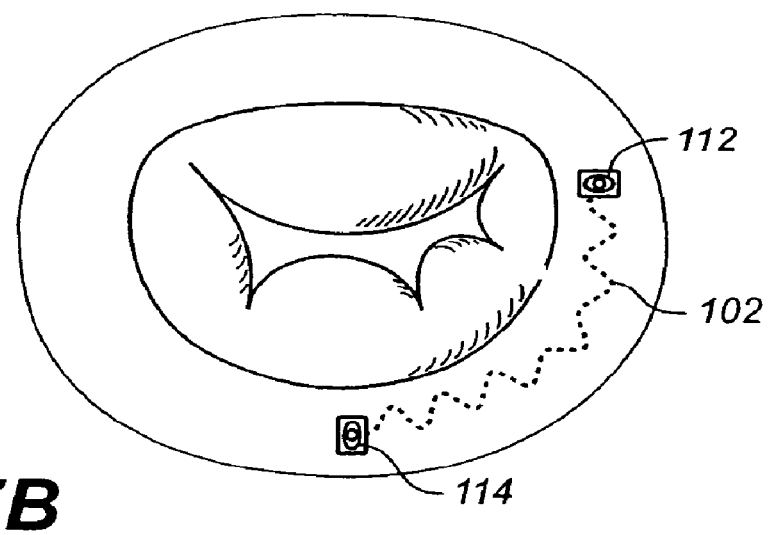
FIG._7B

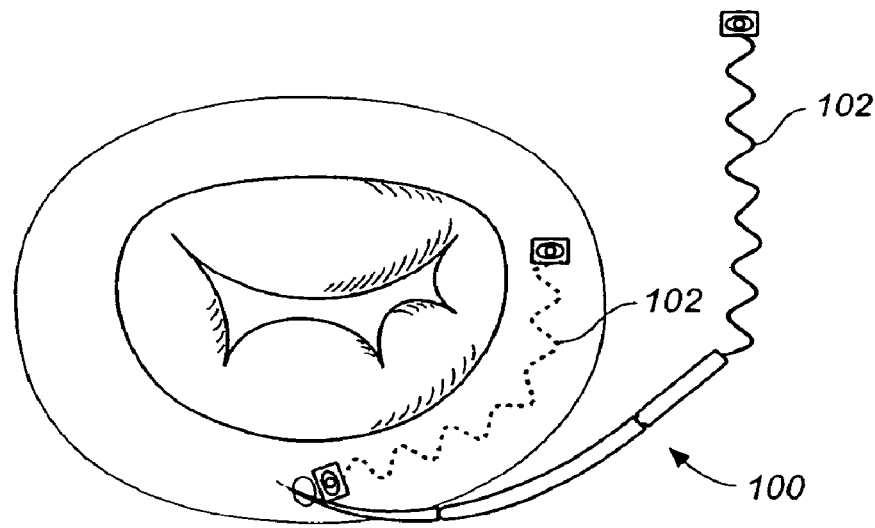
FIG._7C
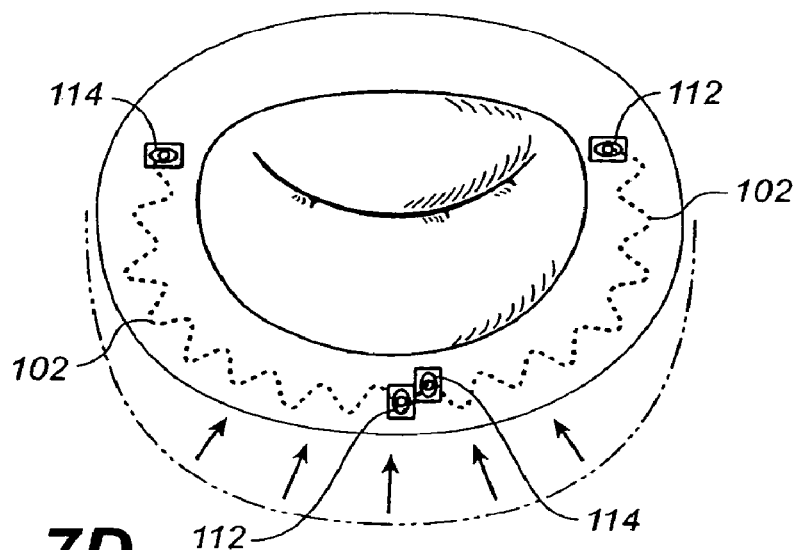
FIG._7D

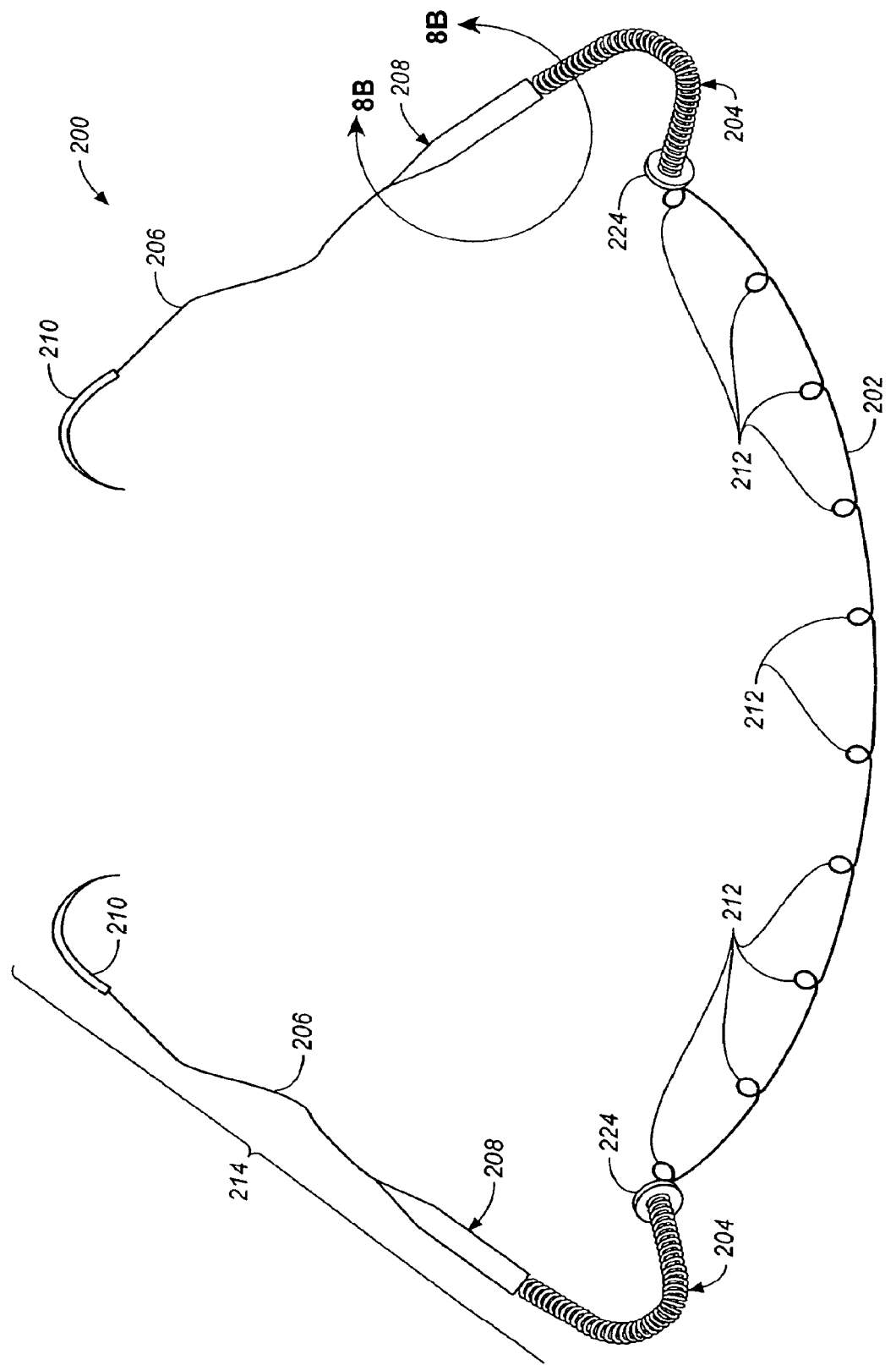

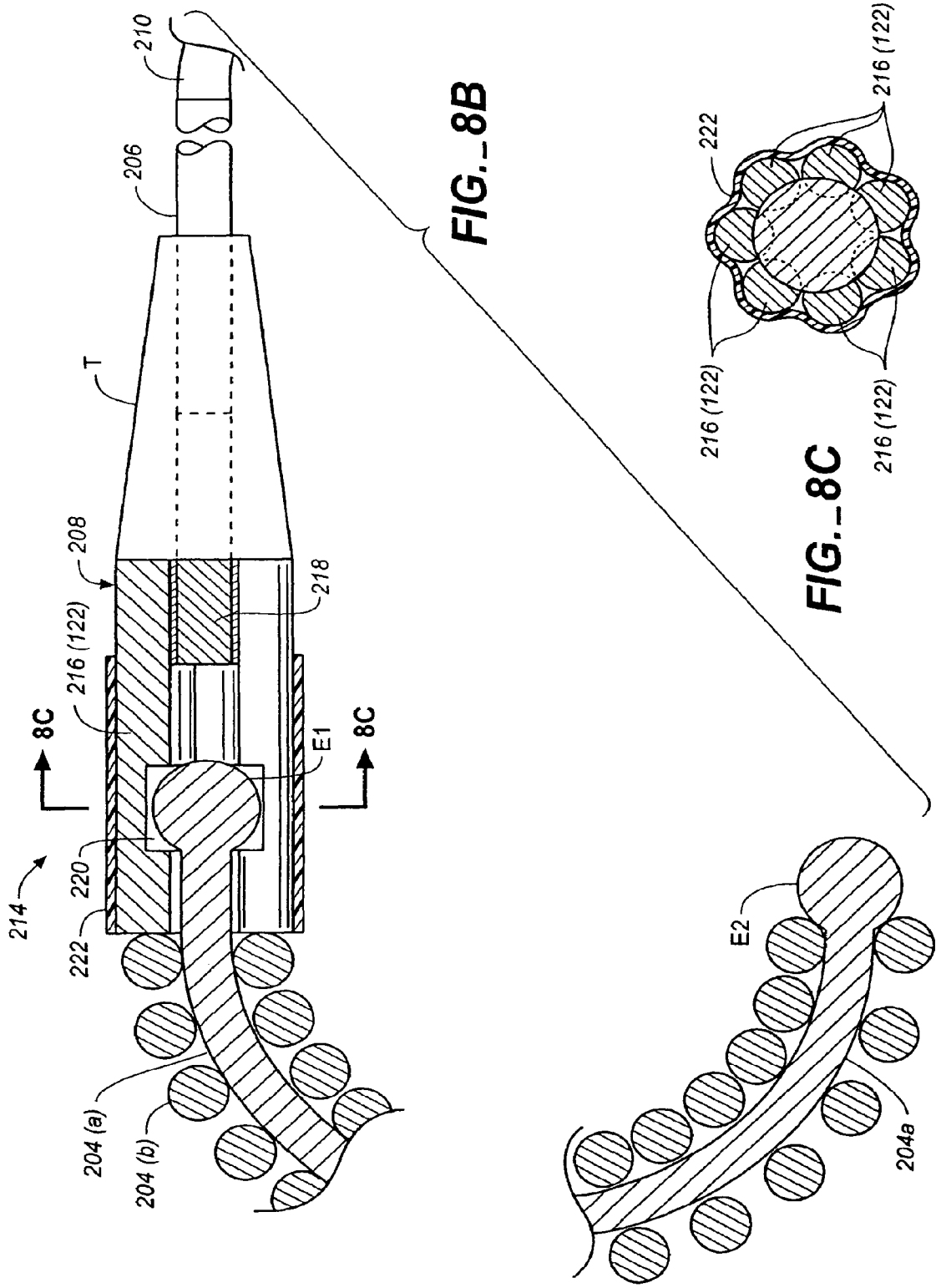

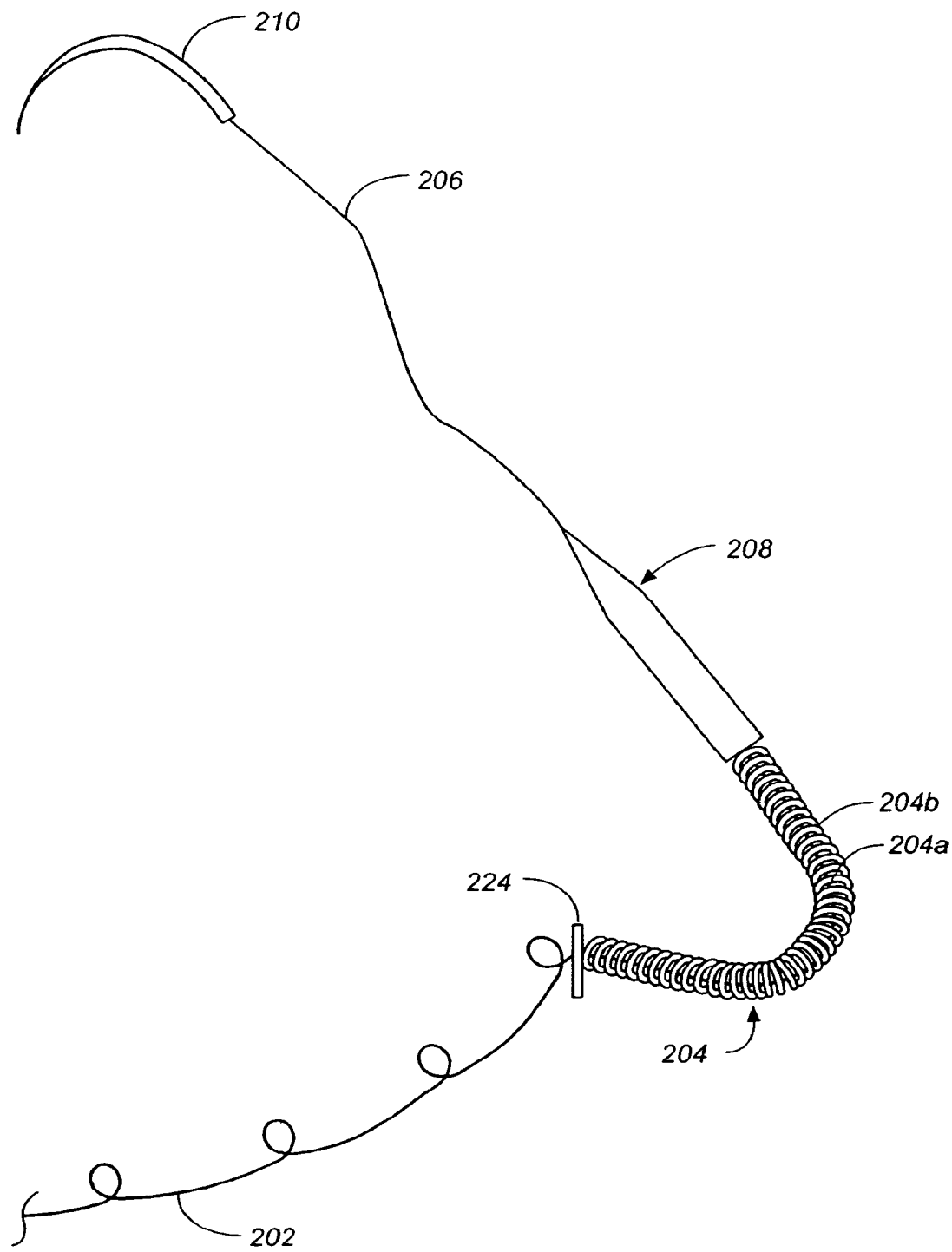
FIG._9

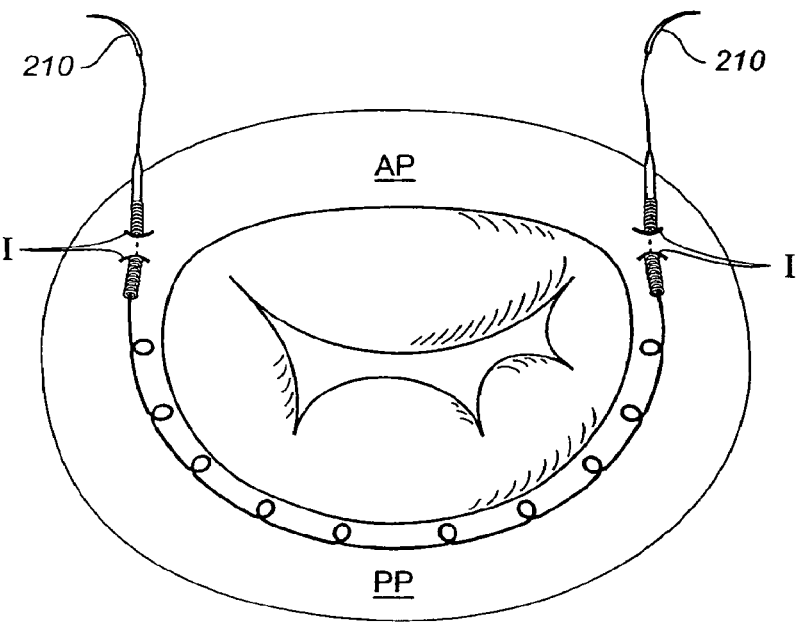
*FIG._10A*
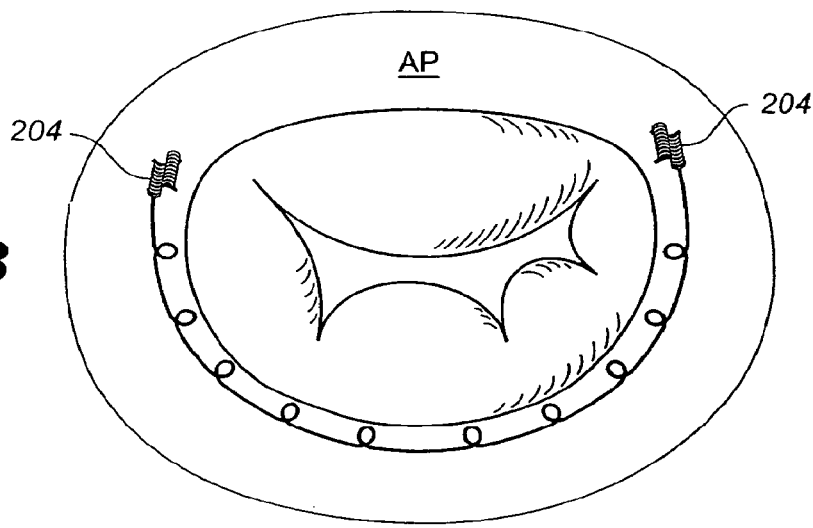
*FIG._10B*
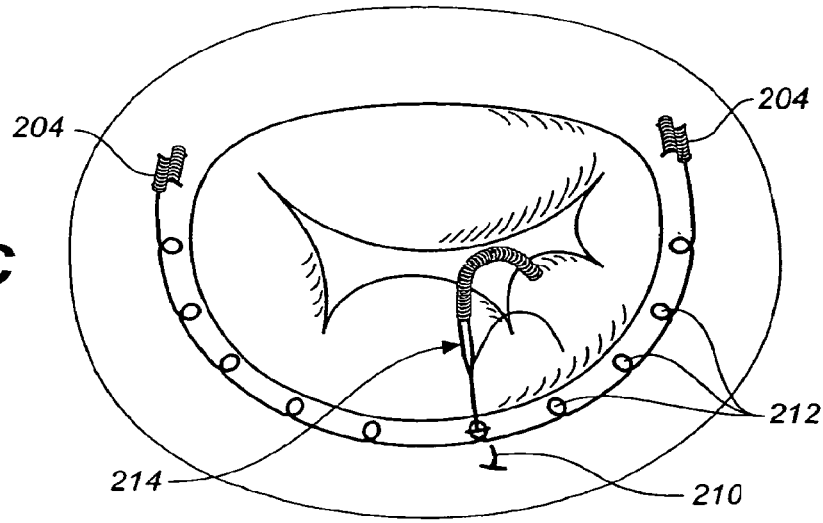
*FIG._10C*

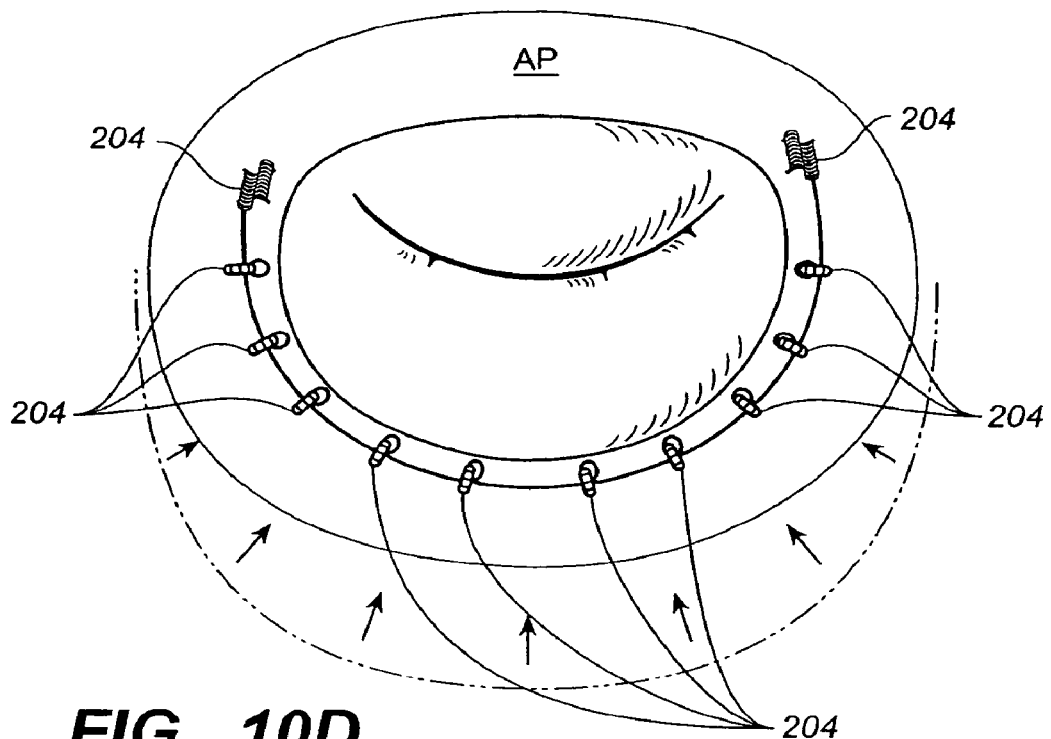
FIG._10D
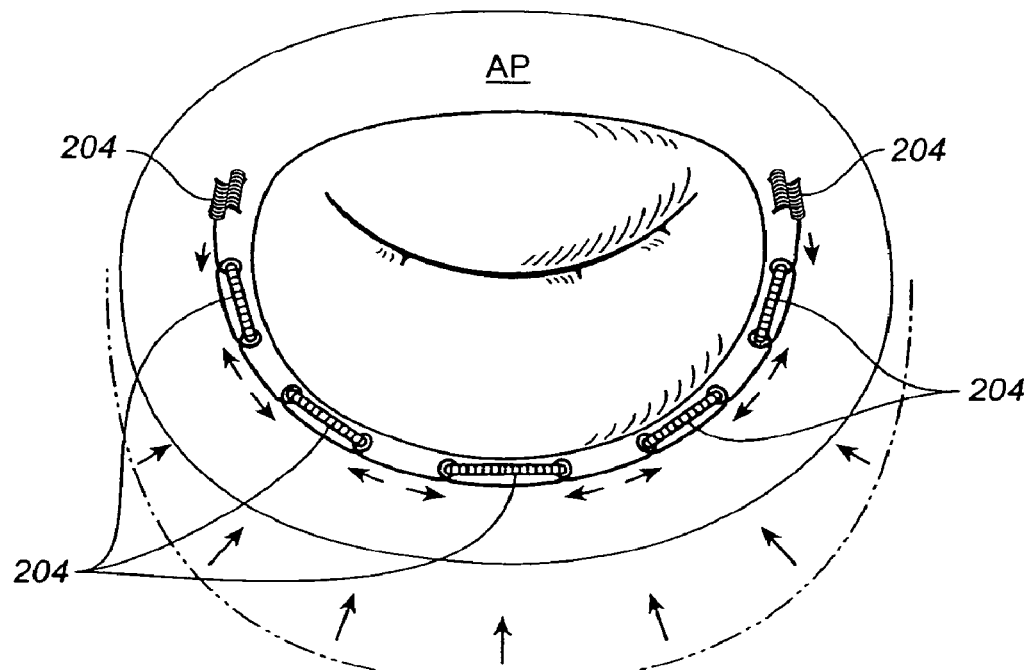
FIG._10E

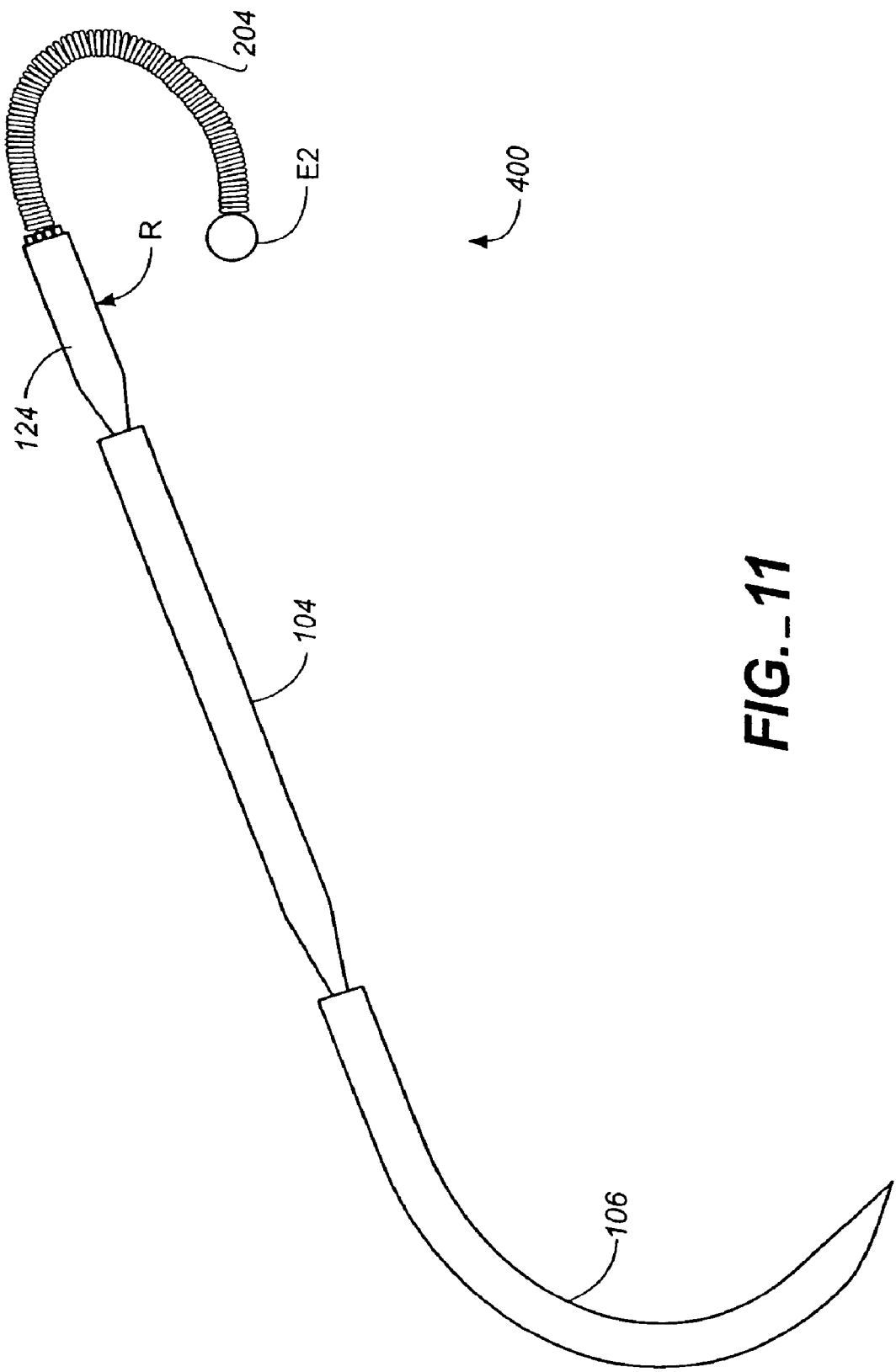
FIG._11

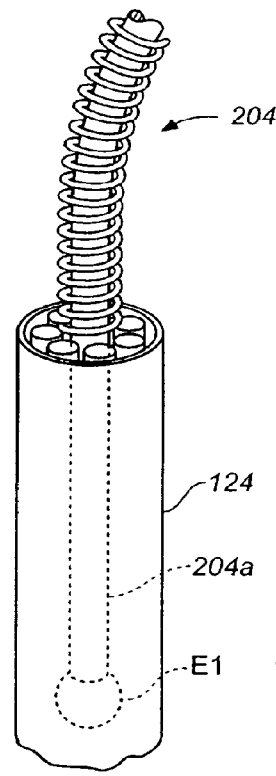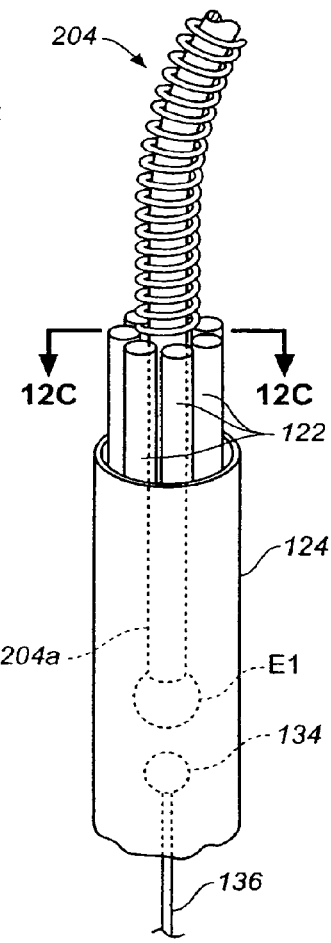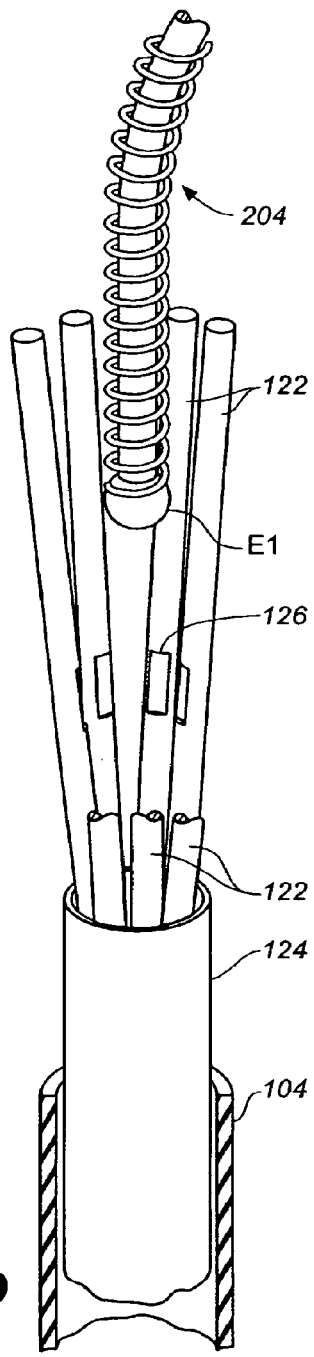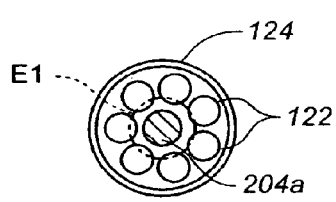
FIG._12A
FIG._12B
FIG._12C
FIG._12D

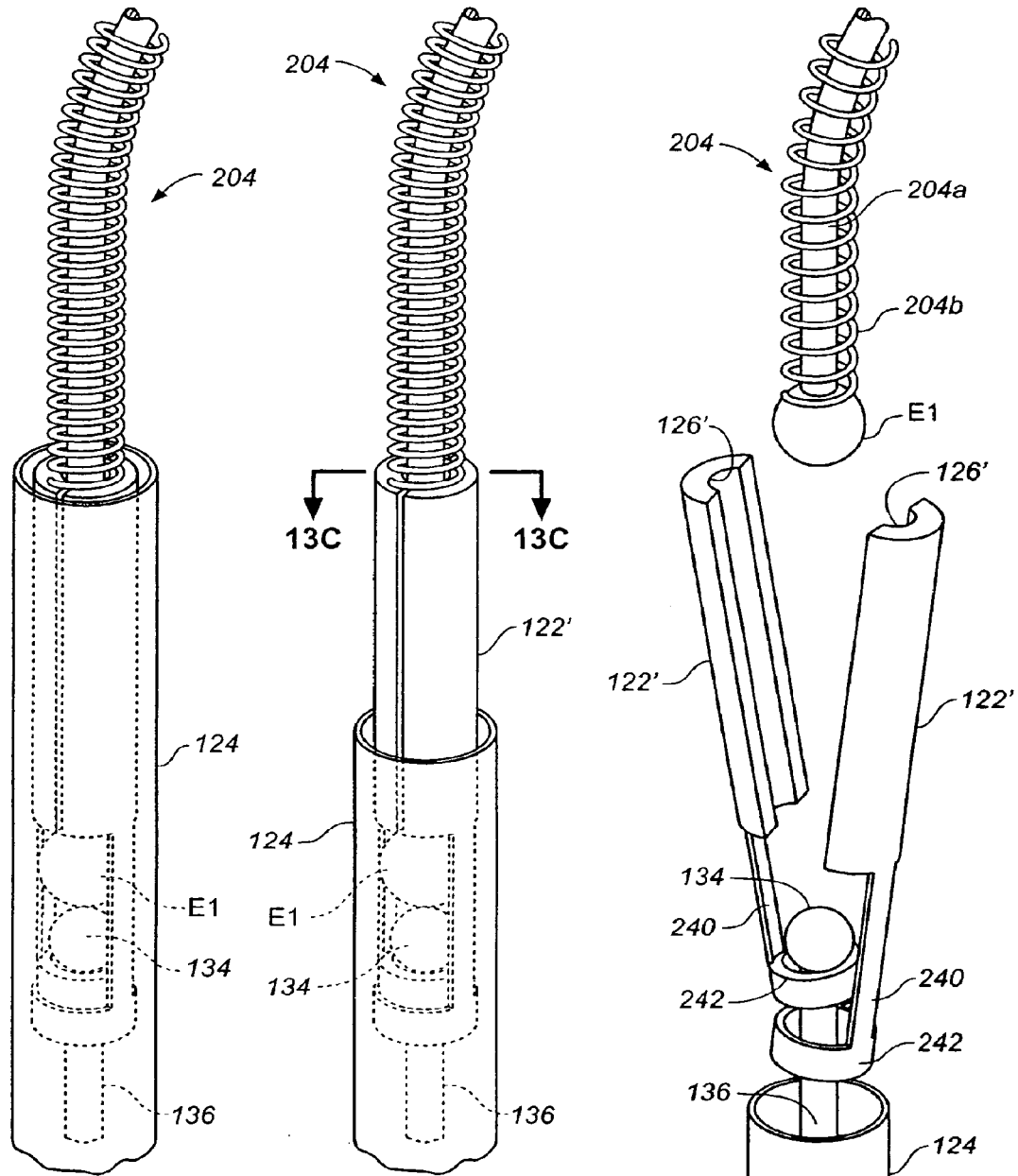
FIG._13A  FIG._13B
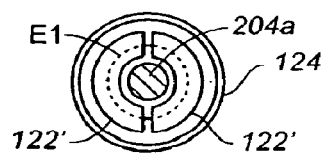
FIG._13C
FIG._13D

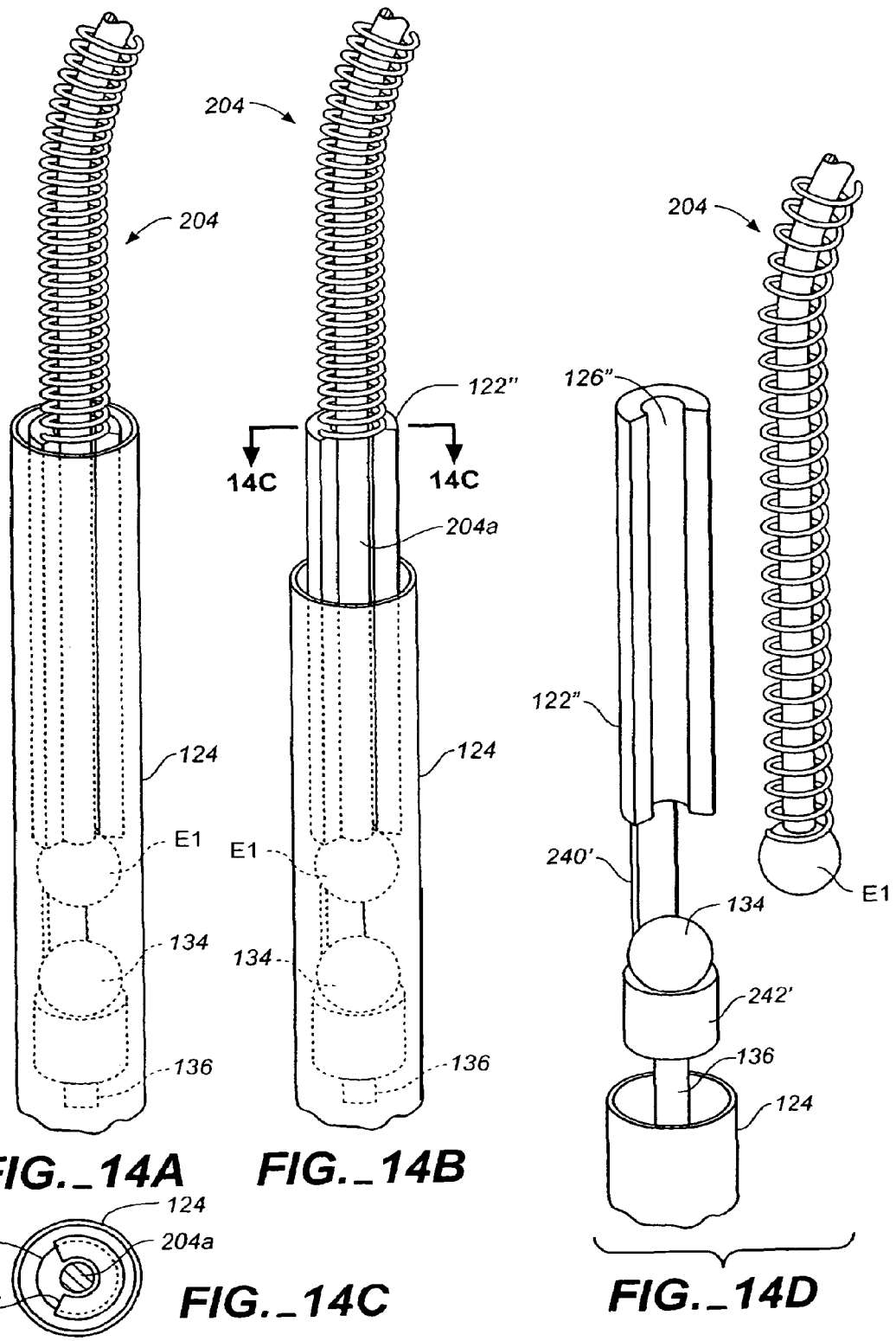

ANNULOPLASTY APPARATUS AND METHODS

CROSS-REFERENCE TO RELATED APPLICATIONS

This application is a continuation of U.S. patent application Ser. No. 10/985,768, filed Nov. 10, 2004, entitled "Annuloplasty Apparatus and Methods", now abandoned, which is a continuation of U.S. patent application Ser. No. 10/125,811, filed Apr. 18, 2002, entitled "Annuloplasty Apparatus and Methods", now abandoned; the entire teachings of both of which are incorporated herein by reference.

FIELD

The disclosure relates to heart valve repair and particularly to annuloplasty apparatus and methods. The disclosure is especially useful in mitral valve annuloplasty procedures, which generally involve mitral insufficiency (e.g., regurgitation when the mitral valve does not properly close).

BACKGROUND

Essential to normal heart function are four heart valves, which allow blood to pass through the four chambers of the heart in one direction. The valves have either two or three cusps, flaps, or leaflets, which comprise fibrous tissue that attaches to the walls of the heart. The cusps open when the blood flow is flowing correctly and then close to form a tight seal to prevent backflow.

The four chambers are known as the right and left atria (upper chambers) and right and left ventricles (lower chambers). The four valves that control blood flow are known as the tricuspid, mitral, pulmonary, and aortic valves. In a normally functioning heart, the tricuspid valve allows one-way flow of deoxygenated blood from the right upper chamber (right atrium) to the right lower chamber (right ventricle). When the right ventricle contracts, the pulmonary valve allows one-way blood flow from the right ventricle to the pulmonary artery, which carries the deoxygenated blood to the lungs. The mitral valve, also a one-way valve, allows oxygenated blood, which has returned to the left upper chamber (left atrium), to flow to the left lower chamber (left ventricle). When the left ventricle contracts, the oxygenated blood is pumped through the aortic valve to the aorta.

Certain heart abnormalities result from heart valve defects, such as valvular insufficiency. For example, mitral valve insufficiency, also known as mitral regurgitation, is a common cardiac abnormality where the mitral valve leaflets do not completely close when the left ventricle contracts. This allows blood to flow back into the left atrium, which then requires the heart to work harder as it must pump both the regular volume of blood and the blood that has regurgitated back into the left atrium. Obviously, if this insufficiency is not corrected, the added workload can eventually result in heart failure.

One option to correct valve defects is complete valve replacement. This intervention, however, is quite invasive and traumatic. There are more conservative surgical interventions that are less traumatic than implanting valvular prostheses. These approaches include valve leaflet repair, chordae tendinae shortening or replacement, and or valve annulus repair also known as annuloplasty. One example where annuloplasty procedures have been developed is in the field of mitral valve insufficiency correction.

Mitral valve insufficiency typically results from a change in the size and shape of the mitral valve annulus. Mitral valve annuloplasty involves reestablishing the normal shape and size of the mitral valve annulus so that it can effect full closure of the valve leaflets.

There have been a number of annuloplasty approaches to repair the mitral annulus of a patient's heart. Dr. Norberto G. De Vega developed a procedure in the early 1970s. One laces a suture along the periphery of a compromised portion of the heart valve. The suture is drawn in a "purse string" manner to cinch the tissue and reduce the size of the valve opening. Then the suture ends are knotted. Although the procedure can reduce the size of the valve opening and improve valve efficiency, it is not free from drawbacks. One disadvantage of this approach is that the sutures can pull out of the tissue and "guitar sting" across the valve annulus. The purse string also may cause tissue bunching, which may distort the natural shape of the valve.

Other approaches to improve valve function (e.g., with the mitral or tricuspid valves) include tissue plication devices and reinforcement of the valve annulus with annuloplasty rings. These approaches also are claimed to reestablish the original annulus size and shape and/or prevent further annulus dilation.

Both rigid and flexible annuloplasty rings have been developed. Rigid rings, which generally tend to dictate the shape and contour of the mitral valve annulus, have been considered to somewhat compromise the natural flexibility of the annulus. Flexible annuloplasty rings emerged to provide some degree of compliance in the valve annulus so that the valve could maintain normal physiological motion throughout the cardiac cycle of a beating heart. This is in addition to providing annulus reinforcement. However, it is believed that among the drawbacks of these rings is that they may fold or crimp during implantation and thereby undesirably reduce the size of the valve (e.g., mitral) opening. Also, the sutures used to secure the ring may cause scarring and stiffening of the valve annulus and reduce annulus flexibility over time.

C-shaped bands or partial annuloplasty rings also have been developed. These devices can be attached solely to the posterior portion of the valve annulus which eliminates the need to attach material to the anterior portion of the annulus. The annulus is fibrous and generally does not require plication and/or reinforcement. Thus, the partial rings can preserve the normal function of the anterior portion of the annulus. Full and partial ring devices are disclosed, for example, in U.S. Pat. No. 3,656,185, which issued to Carpentier.

Other attempts to improve upon valve repair procedures, including the De Vega approach and the use of rigid, flexible, and partial rings, include that described in U.S. Pat. No. 5,450,860, which issued to O'Connor, U.S. Pat. No. 6,183,512B1, which issued to Howanec, Jr. et al., and U.S. Pat. No. 6,250,308B1, which issued to Cox.

The O'Connor patent discloses a plication approach, particularly suitable for use with an annuloplasty operation on heart valves (e.g., mitral or tricuspid valves). The approach involves a ligament, which can comprise a wide, flexible strip of expanded polytetrafluorethylene or similar material, and sutures to retain the ligament in place. The ligament has at least an end of constricted diameter and a needle attached thereto, or it can have two constricted ends and a needle attached to each of the ends. This construction permits the ligament to be drawn through an area of tissue to be plicated. Once in place, a first end of the ligament is anchored, preferably with sewing of conventional sutures through the ligament, and the tissue is cinched along the length of the ligament to provide the desired amount of plication. Once the tissue is correctly oriented, the second end of the ligament is then likewise anchored in place, again preferably through the use of a suture sewn through the ligament.

The Howanec patent describes a system that includes an elongate flexible band with a needle attached to one end of the band and a fit adjuster attached to the other end of the band. The needle is used to introduce the band into the atrioventricular groove (hereafter "AV groove") and then pull a portion of the band out of the tissue. After the band is so implanted into the AV groove, a fit adjuster is used to couple the exposed ends of the band and size and position the band in the annulus. After the band is pulled to cinch the tissue in the AV groove until the valve annulus is reconfigured to an optimal shape, the band can be secured to the valve annulus with sutures and the exposed portions of the annuloplasty system removed.

The Cox patent describes a system that comprises a combined annuloplasty ring implant, which has a rigid section and a flexible section. A needle is coupled to one end of the implant. The needle facilitates introducing the implant into the fatty pad of the AV groove, which surrounds the valve annulus, at one end of the posterior portion of the annulus and pulling one end portion of the implant out of the AV groove in the vicinity of the other end of the posterior portion of the annulus. The flexible section of the ring extends adjacent to the flexible posterior portion of the annulus, while the rigid section of the ring spans the substantially rigid inter-trigone section of the annulus. Cox advances that with this procedure one need not suture the flexible section directly to the mitral valve annulus, thereby substantially eliminating scarring and stiffening of the annulus. In one example, the flexible material is also elastic to accommodate the expansion and contraction of the annulus, in addition to flexing. The system further includes means for joining the ends of the ring, which are positioned along the inter-trigone section, after the needle is removed. Sutures can be added to secure the annuloplasty ring to the annulus, for example, along the inter-trigone section.

Other plication and valve repair approaches are disclosed in PCT International Patent Application Nos. PCT/US01/42653 and PCT/US01/31709, which are co-owned by the assignee of the present disclosure and entitled "Minimally Invasive Annuloplasty Procedure and Apparatus" and "Minimally Invasive Valve Repair Procedure and Apparatus," and which published under International Publication Nos. WO 02/30298 and WO 0230295, respectively. These approaches, in-part, address various inherent disadvantages with prior open heart surgical procedures as described, for example, by F. Maisano, et al. in their article entitled "The double-orifice technique as a standardized approach to treat mitral regurgitation due to severe myxomatous disease" which appeared in European Journal of Cardio-thoracic Surgery, Vol. 17 (2000) 201-205. Disadvantages associated with such open-heart procedures include cumbersome suture management, timely knot tying steps, pain, and long recovery time.

Generally, known annuloplasty ring and band recipients are required to undergo anticoagulation therapy for a minimum of several months post-operatively due to the high risk of prosthesis-induced thrombosis. However, anticoagulation therapy increases the risk of bleeding complications due to the inhibition of blood clot formation.

Applicants believe that there remains a need for improved valvular repair apparatus and methods.

SUMMARY

The present disclosure involves annuloplasty systems that avoid problems and disadvantages of the prior art. The present disclosure involves an annuloplasty system for repairing a valve in a patient's heart. The system comprises a surgical implant, which includes a member having first and second end portions. The implant member further is configured and/or adapted to form a partial ring along a portion of one of the valve annulae of a patient's heart such as the mitral or tricuspid valve annulus. The implant member is axially elastic such that it can axially expand and contract and includes first and second anchors extending from the end portions of the implant member to anchor the implant in tissue such as the mitral or tricuspid valve annulus. The system can facilitate tissue plication (e.g., of the posterior annulus of the mitral valve or the anterior annulus of the tricuspid valve) and reinforcement of a valve annulus.

The partial ring configuration may reduce or minimize the risk of stenosis as compared to more bulky systems using full rings. This configuration also can reduce the amount of prosthetic material that is exposed to blood flow, thus, minimizing or eliminating the requirement for post-operative anticoagulation. Further, since the ends are not joined, the surgeon need not place anything on the anterior portion of the annulus (in the case of mitral valve repair), which otherwise could obstruct flow intake.

According to another aspect of the annuloplasty system, clips can be used in lieu of sutures to anchor or fasten the implant in the desired position. This eliminates cumbersome suturing approaches, simplifies implantation as compared to conventional methods, and facilitates minimally invasive (e.g., endoscopic) approaches to valve annuloplasty (e.g., mitral or tricuspid valve annuloplasty).

According to one embodiment of the disclosure, the implant member has a small cross-sectional dimension, but it is curved to form an implant of much greater overall transverse dimension or diameter. In this embodiment, the implant member can comprise a wire formed to have, for example, an undulating configuration adapted for implantation within the valve annulus. The implant wire with a wire diameter, for example, can range from about 0.002 to 0.062 inches, yet have an overall transverse dimension (measured from peak to trough) of about 0.010 to 0.375 inches. Preferably, the overall transverse dimension, which also may be described as the width or amplitude of the undulating member, taken along a portion of the implant is about 5 to 10 times greater than the implant wire diameter. This construction facilitates implant stability and proper implant orientation with respect to the annulus, while minimizing implant bulk, which, in turn, can reduce or eliminate the risk of prostheses induced thrombosis.

The curved wire construction of the present disclosure also can be configured to provide desirable flexibility so that the implant can comply with annulus flexure during normal cardiac function. The implant also can be configured to be axially elastic or compliant. With such axial elasticity, the implant can expand and contract to accommodate annulus expansion and contraction during relaxation (i.e., expansion) and contraction of the left ventricle.

According to a further embodiment of the disclosure, the implant member can comprise a wire formed to have a plurality of loops formed therein. Anchors or sutures can be attached to the loops and tissue to secure the implant member to the tissue. The wire diameter typically is about 0.002 to 0.062 inches and the diameter of the loops preferably range from about 0.010 to 0.050 inches. As the annulus is secured to the loops, it conforms to the implant shape, which can be configured to reshape the annulus toward or to its original size and shape to improve or correct cardiac function.

According to a further aspect of the disclosure, a needle can be releasably coupled to one end of the implant. The needle simplifies implant delivery and avoids the need for time-consuming suture procedures.

The above is a brief description of some deficiencies in the prior art and advantages of the present disclosure. Other features, advantages, and embodiments of the disclosure will be apparent to those skilled in the art from the following description, accompanying drawings, wherein, for purposes of illustration only, specific forms of the disclosure are set forth in detail.

BRIEF DESCRIPTION OF THE DRAWINGS

FIG. 1A is a perspective view of an annuloplasty system constructed in accordance with the present disclosure.

FIG. 1B is a longitudinal sectional view of the annuloplasty system depicted in FIG. 1.

FIG. 1C is a variation of the annuloplasty system of FIG. 1.

FIGS. 2A, 2B, 2C, and 2D diagrammatically show release of the implant illustrated in FIG. 1.

FIG. 3A is a perspective view of the pivotally mounted retainer illustrated in longitudinal and transverse positions in FIGS. 2A-2D.

FIG. 3B is an end view taken along line 3B-3B in FIG. 3A.

FIG. 3C is a sectional view taken along line 3C-3C in FIG. 3A.

FIGS. 4A and 4B depict a straight and curved embodiment of the implant shown in FIG. 1A.

FIGS. 5A, 5B, 5C, 5D, and 5E diagrammatically illustrate a method using of the annuloplasty system of FIG. 1.

FIGS. 6A, 6B, 6C, 6D, and 6E diagrammatically illustrate another method of using the annuloplasty system of FIG. 1A.

FIGS. 7A, 7B, 7C, and 7D diagrammatically illustrate a further method of using the annuloplasty system of FIG. 1A.

FIG. 8A shows another annuloplasty system in accordance with principles of the present disclosure.

FIG. 8B is a sectional view of the release mechanism of FIG. 8A taken along line 8B-8B and a surgical slip.

FIG. 8C is a sectional view of taken along line 8C-8C in FIG. 8B.

FIG. 9 diagrammatically illustrates one juncture configuration between one of the surgical clips and the implant member of FIG. 8A.

FIGS. 10A, 10B, 10C, 10D, and 10E show a method of using the annuloplasty system of FIG. 8A.

FIG. 11 is a perspective view of the delivery and release apparatus of FIG. 1 coupled to a self-closing clip such as the self-closing clip of FIG. 8B.

FIGS. 12A, 12B, 12C, and 12D diagrammatically illustrate the operation of one release apparatus for use with the system of FIGS. 1 or 11.

FIGS. 13A, 13B, 13C, and 13D diagrammatically illustrate the operation of another release apparatus for use with the system of FIGS. 1 or 11.

FIGS. 14A, 14B, 14C, and 14D diagrammatically illustrate the operation of yet another release apparatus for use with the system of FIGS. 1 or 11.

DETAILED DESCRIPTION

Referring to the drawings wherein like numerals indicate like elements, FIG. 1 illustrates an annuloplasty system 100 constructed in accordance with the principles of the disclosure. Annuloplasty system 100 generally comprises an implant member 102, a flexible member 104, and a needle 106. In the illustrated embodiment, system 100 also includes anchors or stoppers 112 (FIG. 1A) and 114 (FIG. 1B) and a release mechanism 108 to releasably couple the implant to the flexible member.

The distal end of the implant member may have an enlarged portion 110 as shown in the drawings. A stopper or anchor 112, preferably in the form of a disc and preferably welded to the distal end of the implant member, may be provided adjacent to the enlarged portion 110. Similarly, another stopper or anchor 114 may be provided adjacent to the implant's proximal enlarged portion 116 as shown in FIG. 1B. Stopper or anchors 112 and 114 also may referred to as retainers. Stopper 114 will be described in further detail in the discussion of FIGS. 2A-2D and 3A-3C. Pledgets 118 and 120 (see e.g. FIG. 2B), which may comprise any suitable material such as TEFLON® polytetrafluoroethylene material or DACRON® synthetic polyester textile fiber, also may coupled to the implant adjacent to the stoppers to minimize or eliminate the risk of having the implant tear the tissue in which is it embedded.

Referring to FIG. 1B, release mechanism 108 generally includes a plurality of arms or cables 122, which releasably engage enlarged portion 116 of implant 102, and a sleeve 124 that retains the arms 122 in a closed configuration such that enlarged portion 116 is locked or secured therein. Arms 122 have notches 126 and 128 (FIG. 2D) formed therein to form inner annular grooves 130 and 132, respectively. Annular groove 130 holds or retains enlarged portion 116 and annular groove 132 holds or retains enlarged portion 134, which is formed on the end of cable or wire 136, which, in turn, is secured to needle 106. A band 138 is fit into an outer annular channel 140 (FIG. 2C), which is formed by forming notches 142 in the outer surface of cables or arms 122. Band 138 retains the portion of the bundle of cables or arms 122 adjacent thereto tightly together so that enlarged portion 134 remains secured therein.

A flexible tubular member 104 is provided between needle 106 and release mechanism sleeve 124. Specifically, one end of tubular member 104 receives one end of release mechanism sleeve 124. Release mechanism sleeve 124 is sufficiently flexible so that it can slide within tubular member 104 as it is retracted or removed from the bundle of cables or arms 122 to release enlarged portion 116 and, thus, implant member 102 as will be described in more detail below. The other end of tubular member 104, together with the end of wire 136 is inserted in a recess 146 (FIG. 1B) formed in the needle and secured therein such as by swaging.

Referring to FIG. 1C, a variant of the system illustrated in FIG. 1B is shown where tubular member 104 is eliminated and the tubular sleeve 124 of the release mechanism 108 is directly coupled to the needle. In this embodiment a needle 106' is formed with a deep recess 146' so that release mechanism sleeve 124 can sufficiently slide into the recess and be sufficiently removed from the cable bundle to release enlarged portion 116 and, thus, implant 102.

Returning to the embodiment of FIGS. 1A and 1B, FIGS. 2A-2D sequentially depict release of implant member 102, which in the illustrated embodiments includes straight portion 102(a) and undulating portion 102(b) the length of which are indicated in FIG. 2D with reference characters "a" and "b," respectively. After the implant member is positioned in the desired location, the surgeon or assistant can slide pledget 120 over needle 106, tube 104, and release mechanism 108 (FIG. 2A) so that it can be positioned adjacent to undulating portion 102(b) of the implant prior to actuating release of the implant member (FIG. 2B). Sleeve 124 is retracted and drawn into tubular member 104 first releasing pivotally mounted stopper or anchor 114, which also may be referred to as a retainer, so that it may pivot to a transverse position relative to the wire of which the illustrated implant comprises. As sleeve 124 is further retracted, it releases arms 122 of release mechanism 108, which in turn release enlarged portion 116 of implant member 102 (FIG. 2D). Since sleeve 124 biases arms 122, which normally assume the radially outward expanded configuration shown in FIG. 2D, to the closed configuration shown in FIGS. 2A-C, the arms open as shown in FIG. 2D when sleeve 124 is retracted.

Referring to FIGS. 3A-C, proximal stopper or anchor 114, which also may be referred to as a retainer, is shown in further detail. Stopper 114 can be formed from a tube by removing two half tubular sections as shown in the drawings. One can remove one half tubular section along one section of the tube and another half tubular section along another section of the tube on the other side thereof as illustrated in FIGS. 3A-C. As shown, surfaces 114(a) and 114(b) can be angled to simplify the material removal process in forming stopper 114.

Although a particular implant configuration has been shown, other configurations can be used without departing from the scope of the disclosure. Referring to FIG. 4A, undulating portion 102(b) of implant 102 can comprise a wire, which is formed so that it is generally two-dimensional (flat or planar) and straight as previously shown prior to implantation. Alternatively, a curved, arc-shaped, or crescent shaped undulating wire member that is generally two-dimensional (flat or planar) can be used for implantation as shown in FIG. 4B. These configurations afford orientation stability when embedded in a mitral valve annulus, for example and as will be further described below, while minimizing the size or bulk of the implant. It is believed that the reduced valve implant bulk can reduce the risk of thrombosis. Although the undulating portion also may be formed so that it has two and three dimensional portions or so that it is entirely three dimensional, the two dimensional variation is believed to offer optimal stability.

The wire diameter can vary from application to application. For example, when applied to normal human mitral valves, it can range from about 0.002 to 0.062 inches, more preferably in the range of about 0.005 to 0.015 inches, and typically will be about 0.089 inches. The wire diameter range is the same when applied to tricuspid valves. The transverse dimension or width "W" (FIG. 2C) of the undulating member can range from about 0.010 to 0.375 inches and thus can be 5 to 10 times greater than the wire diameter. The implant length also can vary depending on the application. When used for mitral annuloplasty, it is embedded in the annulus from one trigone to the other trigone. Therefore, its length ranges from about 25 to 85 mm when applied to normal adult human mitral valves. When applied to human tricuspid valves it is implanted along the posterior annulus and extends in a circumferential direction from trigone to trigone, and its length can be in the same ranges.

The implant or implant wire preferably comprises a shape memory alloy or elastic material. As is well known in the art, shape memory material has thermal or stress relieved properties that enable it to return to a memory shape. When stress is applied to shape memory alloy material causing at least a portion of the material to be in its martensitic form, it will retain its new shape until the stress is relieved. Then it returns to its original, memory shape. On the other hand, when shape memory material is cooled to where it is in its martensitic form and then deformed, it retains the deformed shape until its temperature is increased so that the material becomes austenitic. Then it returns to its original, memory shape. One preferred shape memory material for the implant member is nitinol.

The shape memory wire (e.g., nitinol) can be shape set into the undulating configuration by weaving the wire through a fixture having a row of rods and affixing the two ends of the nitinol wire under tension. Alternatively, the nitinol wire can be shape set by press molding using a mold with a crimped pattern. The heat treatment to permanently set the shape of the nitinol wire can be achieved by heat-treating in either a convection oven or bath at a temperature range of 100 to 600° C. for a duration of 2 to 20 minutes. In assembling the system the distal stopper can be welded to one end of the shape set embedded wire. The retractable stopper is loaded onto the proximal end of the embedded wire. A ball is formed onto the proximal end of the embedded wire by welding. The release mechanism is assembled with a flexible member and a taper component to transition from the flexible member to the release mechanism. The release mechanism is attached to the ball of the embeddable wire at the proximal end and the retractable stopper is placed into its retracted position within the release mechanism component. Then, a needle is swaged onto the flexible member.

Referring to FIGS. 5A-5D, an exemplary method of using annuloplasty system 100 for mitral valve annuloplasty is shown in accordance with the present disclosure. As noted above, a competent mitral valve (MV) allows one-way flow of oxygenated blood that has entered the left atrium from the lungs to enter the left ventricle. The left ventricle then pumps the oxygenated blood to the rest of the body.

Referring to FIG. 5A, the mitral valve (MV) comprises a pair of leaflets, the anterior leaflet (AL) and the posterior leaflet (PL) of which the latter is larger. The base of each leaflet is attached to the mitral valve annulus (MVA). The mitral valve annulus includes a posterior portion (PP) and an anterior portion (AP) also known as the inter-trigone section, which is a generally straight substantially rigid section. The posterior portion of the annulus is a flexible, curved section that encompasses a larger portion of the annulus circumference than the anterior portion. The right and left fibrous trigones (generally indicated with reference characters RT and LT) mark the end of the generally straight section (inter-trigone section) and define the intersection points between the posterior and anterior portions (PP, AP).

The leaflets open and close in response to pressure differences on either side of thereof. However, when the leaflets do not fully close, regurgitation and valve insufficiency can result. One method to treat the insufficiency using the annuloplasty system of FIG. 1 will be described with reference to FIGS. 5B-5E.

Referring to FIG. 5B, needle 106 of annuloplasty system 100 is passed through the endocardium and the left atrial myocardial wall and into the right fibrous trigone (RT). The needle is then moved in a clockwise direction through the fibrous structure of mitral valve annulus toward the left fibrous trigone (LT). At the left fibrous trigone (LT), the needle is passed back through the left atrial myocardial wall from the epicardium and back through the endocardium at the left fibrous trigone (FIG. 5C). The needle is further drawn from the annulus until the release mechanism is fully withdrawn from the annulus and above the tissue surface. This preloads the implant wire and plicates the annulus. Pledget 120 is drawn over the needle and slid over the flexible member and release mechanism and then positioned between the undulating implant member and the release mechanism as described above. The surgeon withdraws sleeve 124, thereby releasing implant member 102 from the release mechanism 108, flexible member 104, and needle 106, and deploying proximal retainer or anchor 112 so that it opens to its active position as previously shown in FIGS. 2C and 2D and here in FIG. 5E where both retainers or anchors are firmly set at the fibrous trigones. Alternatively, the needle can be introduced through the left fibrous trigone and withdrawn from the right fibrous trigone.

Referring to FIG. 5E, the undulating wire is fully embedded within the valve annulus with the anterior and posterior leaflets restored in a sealed configuration. The only non-embedded, blood contacting components are the anchors or retainers 112 and 114, which are positioned at the two fibrous trigones (RT, LT). Due to the implant wire's undulating configuration, the wire can be elongated in the axial direction. In the elongated condition (partially in FIG. 5C and fully in FIG. 5D), the wire, which has shape memory to regain its original unloaded length, applies a recoil force to draw the two ends of the implant together in the axial direction. In the implanted condition where the undulating wire is stressed to an elongated configuration by threading through the tissue, the shape memory force draws the annulus together resulting in tissue plication and a reduction in annulus size (FIG. 5E). In sum, the procedure generally provides annuloplasty plication and reinforcement, while maintaining annular compliance.

Referring to FIGS. 6A-6E, a variation on the procedure described above is illustrated. This procedure is the same as that shown in FIGS. 5A-5E with the exception that needle 106 is not drawn through the entire posterior annulus in a single pass. In this case, the surgeon makes multiple bites (see FIGS. 6B and 6C) with the needle to cover the distance of the posterior annulus. The procedure is completed in the same way as that described above (FIGS. 6D & E are the same as FIGS. 5D & E).

Referring to FIGS. 7A-7D, a further variation on the procedures described above is illustrated. In this procedure, multiple undulated implants are used to span the length of the posterior annulus. In this example, two implants are used to span the annulus. The initial needle penetration occurs at either fibrous trigone. A needle bite length segment of wire is terminated with each needle bite resulting in the plication of discrete sections of the annulus. Subsequent wire segments are penetrated at and are linked to the terminating distal retainer 112. In this manner, separate, but joined wire segments span the posterior annulus to the opposite fibrous trigone resulting in the plication of the entire posterior annulus and reduction in annular size.

In the embodiments described above, the implant member returns to its memory shape upon stress release (i.e., actuation of release mechanism 108). As the implant is inserted, the tissue and pulling forces placed on the device to pull it into position cause it to axially expand. Once in position, the release mechanism is actuated, thereby removing the pulling force and allowing the implant to axially contract toward its memory shape.

Alternatively, the device can be designed to have thermal properties to return to its memory shape at a predetermined temperature. It can be deformed at a first temperature to generally remove or reduce the amplitude(s) or period(s) of the undulations and then inserted into the tissue. After insertion, its temperature rises to the predetermined temperature and it assumes its original, undulating memory configuration. As it returns to its memory shape, it axially contracts and decreases the circumferential dimension of the valve annulus.

Although particular configurations have been illustrated, other configurations can be used without departing from the scope of the disclosure. For example, the wire can be flat. The undulations can have varying or changing amplitude or frequency. The radius of the crests and troughs also can vary from implant to implant or within a single implant. Further, the implant wire can be a single length of wire as shown in the drawings or it can be made up of multiple lengths of wire joined together.

The undulating implant can provide high strength and elasticity to material volume (or diameter) ratio. The implant configuration and construction can provide desirable elasticity that allows for physiological motion in the linear direction (annular dilatation) and planar surface. Since the undulating member can be self-terminating at the trigones, it does not require knot tying, connectors, or cutting. The implant can be less traumatic to the annular tissue as compared to other devices. For example, it does not require multiple suture passes. The implant configuration and placement also can minimize the amount of implant surface that comes into contact with blood flow.

Referring to FIG. 8A, another embodiment of the disclosure is shown and generally indicated with reference numeral 200. Annuloplasty system 200 generally comprises an implant member 202, anchors comprising or in the form of surgical clips 204 coupled to ends of implant member 202, flexible members or wires 206, release mechanisms 208, which releasably couple the flexible members to implant member 202, and tissue piercing members or needles 210, which are secured to the flexible members or wires 206.

Implant member 202 can be straight (not shown), or crescent or arc-shaped so as to form a partial ring as shown in FIG. 8A. Implant member 202 has a plurality of attachment loops 212 formed therein such as by folding the wire of which the implant comprises according to this embodiment. Alternatively, loops 212 may be separately formed and secured to implant member 202 by welding, soldering or other suitable process. Preferably, the loops are equidistantly spaced from one another.

With the exception of one of the surgical clip ends being secured to implant member 202, each anchor-clip, release mechanism, flexible member and needle combination forms a tissue connector assembly 214 similar to tissue connector assemblies described in U.S. patent application Ser. No. 09/089,884, now U.S. Pat. No. 6,607,541, and Ser. No. 09/090,305, now U.S. Pat. No. 6,641,593, both filed Jun. 3, 1998 and Ser. No. 09/259,705, now U.S. Pat. No. 6,514,265, and Ser. No. 09/260,623, now, U.S. Pat. No. 6,613,059, both filed Mar. 1, 2000 and International Application Nos. PCT/US99/12563 and PCT/US99/12566 both filed Jun. 3, 1999 and published under International Publication Nos. WO 99/62409 and WO 99/62406, all of which applications and international publications are hereby incorporated by reference herein. Although one tissue connector assembly configuration is shown herein, any other suitable assembly described in the applications cited in the preceding sentence can be used.

The applications cited in the previous paragraph describe tissue connector assemblies having self-closing clips, which can be characterized as having two end points, which tend to come closer together either by elasticity or so-called pseudoelasticity. Such a clip may be made by heat-treating a NiTi wire to a certain temperature and time to have a desired undeformed shape. The surgical clip generally comprises a wire, preferably, comprise shape memory alloy. In the present disclosure, each clip preferably has two end points, an unbiased closed configuration, the ability to be moved or biased to an open configuration, and the tendency to return to the naturally closed memory configuration, which reduces the separation between the two end points as compared to the spaced end point orientation when the clip is in an open configuration.

The aforementioned U.S. and PCT patent applications describe a clip comprising a deformable wire made of a shape memory alloy, which clip can assume a U-shape when in the open configuration and is one example of a suitable clip for this embodiment of the present disclosure.

Such a clip may be deployed, for example, in the form of a single-arm clip assembly as shown in FIG. 8A and designated with reference numeral 214 and as generally described in the aforementioned U.S. patent applications Ser. Nos. 09/089,884 and 09/090,305, and the section of International Application No. PCT/US99/12566 from page 10, line 10 through page 11, line 21, which section and accompanying FIG. 1 is hereby specifically incorporated by reference herein.

The ends of the clip coil 204(b) are constrained with the coil in compression to urge or bias clip wire 204(a) into a generally U-shaped open configuration.

A release mechanism 208, such as disclosed in aforementioned U.S. patent application Ser. No. 09/260,623 (or International Application No. PCT/US99/12566, which published on Dec. 9, 1999 under International Publication No. WO 99/62406 is provided so that clip wire 204(a) can readily be released by squeezing the release mechanism with a surgical instrument. One suitable release mechanism is specifically described in International Application No. PCT/US99/12566 from page 25, line 12 through page 27, line 30 ending with the text "mechanism 23c" (but without the text "such as needle 17 as shown in FIG. 1" on line 27 of page 27) and the referenced figures are hereby incorporated by reference herein. A summary of such a release mechanism is provided below with reference to FIGS. 8B and 8C.

Referring to FIGS. 8B and 8C, release mechanism 208 generally comprises a plurality of substantially rigid strands, cables or wires 216 (which are the same as cables or strands 122 in FIG. 1B). Cables 216 can be metal and are arranged substantially parallel to one another and circularly about a longitudinal axis. The hidden end portions of the strands are coupled to tapered section "T," which is coupled to piercing member needle 210. The strands can be coupled to rod 218, which is fixed to the tapered section. End portions of the strands include notches, which form a chamber 220 for releasably receiving and/or holding enlarged portion "E1" of the clip and/or fastener wire 204(a) which also has an enlarged portion "E2" at its other end to facilitate compression of coil 204(b). According to International Application No. PCT/US99/12566, supra, the notches preferably are placed about 0.015 inches from the free ends of the strands, but this distance can vary depending upon the desired compression on the coil or spring 204(b). A shrink wrap layer 222, preferably in the form of tubing, is provided around at least the free end portions of the strands and the shrink wrap heated to compress against the strands and hold them in place against enlarged wire portion "E1" to effectively hold the enlarged portion captive until the shrink wrap is squeezed, the strands displaced and the enlarged portion released.

Referring to FIG. 9, implant member 202 and the surgical clip can be formed from a single element or wire. In the embodiment shown in FIG. 8A, a single wire forms the surgical clip and implant member 202. When using a surgical clip such as shown in FIG. 8B, there is no enlarged portion E2. Rather, clip wire 204(a) is long enough to form implant member 202. It can also form a similar clip wire at the other end of the implant as well. In place of enlarged portion E2, the wire can be passed through a washer 224 (FIG. 9) or similar device having a hole formed therethrough and the washer secured to the wire by swaging, for example. The washer is placed at a location along the wire to provide the desired compression of coil 204(b). On the other hand, a clip having an enlarged portion E2 can be used and the enlarged portion E2 secured to the implant member 202 by any suitable means such as welding.

According to one method of making the device, the loops and the general curve shape of member 202 are made from the same piece of wire. The loops are formed by wrapping the wire around mandrels. The mandrels are arranged in the general curve shape, thus giving the appearance of loops superposed onto a general curve shape. Wire cross section diameters can range from about 0.002 to 0.062 inches. Loop diameters can range from about 0.010 to 0.050 inches. The radius of curvature of the overall implant member 202, having loops formed therein, can range from about 0.25 to 1.25 inches, but can be made to any radius. The straight-line distance between the ends of the implant member 202 (between washers 224) ranges from about 0.5 to 2.5 inches. The length of the implant member (measured from washer 224 to washer 224) can range from about 0.75 to 3.0 inches. The profile is essentially the thickness of prosthetic material attached to the annulus. The smaller the diameter, the lower the profile. Lower profile may prevent nonphysiological blood flow, which can lead to undesirable hemodynamic effects, e.g., thrombosis, disruption of red blood cells, or slower tissue healing. When the surgical clip is made from the same piece of wire as the multilooped member, the last loop is the one that abuts washer 224, which is passed onto the multiloop member and crimped to act as a stopper for the coil 204(b), which surrounds a portion of the wire that forms the implant member and surgical clip. The release mechanism 208 compresses the coil against washer or constraint 224, which maintains the surgical clip in a U-shaped configuration.

Referring to FIG. 10A-10D, an exemplary mitral valve annuloplasty method using annuloplasty system 200 will be described. In general, implant member 202 is implanted onto the mitral valve annulus of the target mitral valve such that the implant member or wire is attached to the surface of the annular tissue. In this mitral valve annuloplasty example, the implant member or wire is secured along the posterior annulus with the ends of the implant member secured to the annulus at the two fibrous trigones.

Referring to FIG. 10A, the surgeon first secures tissue connector assemblies 214 at the right and left fibrous trigones. This is accomplished by threading needles 210 into the fibrous structure of the annulus and then drawing the needles out from the annulus sufficiently so that anchors 204 extend out from the annulus at incisions "I." A 5-0 needle can be used in this example. Release mechanisms 208 are squeezed to release the anchors 204 from the release mechanisms 208, flexible members 206, and needles 210 and allow the anchors to close as shown in FIG. 10B.

Then discrete or individual tissue connector assemblies 214 are passed through loops 212 (FIG. 10C) and released so that the clips or anchors 204 of the individual tissue connector assemblies close and secure the loops to the tissue as shown in FIG. 10D, which shows inserting clips 204 radially. According to a variation on the described method, the anchors or clips 204 can be inserted circumferentially as shown in FIG. 10E.

The attachment loops provide elasticity and act as torsion springs. The spring properties generally provide elasticity. In the deployed condition, the implant, having shape memory to regain its original unloaded length, applies a recoil force to draw the two ends together along the length of the implant. In the implanted condition where the implant wire is loaded to an elongated configuration, the shape memory force draws the annulus together resulting in tissue plication and a reduction in annulus size. The preloaded condition of the implant wire continues to provide a reinforcement force to prevent further dilation of the valve annulus. Furthermore, the elastic nature of the loops allow for the natural compliance and physiological motion of the annulus.

The low profile characteristic of the implant as compared to conventional annuloplasty rings or bands reduces the amount or volume of prosthetic material that is exposed to blood flow. This can substantially reduce the need for post-operative anti-coagulation therapy.

Although annuloplasty system 200 has been described with self-closing clip type anchors, other surgical clips can be used as anchors such as that disclosed in U.S. Pat. No. 5,972,024, which issued to Northrop, III et al. Further, sutures can be used to form the anchors as will be discussed in more detail below.

Although a particular system embodiment having two clip anchors, release mechanisms, and delivery needles has been described and illustrated in FIGS. 8A-C, variations of this system can be made within the scope of the disclosure. For example, only one clip anchor, release mechanism, and delivery member may be used. In this case, the clip anchor with its release mechanism and delivery needle can be coupled to one end of the implant member as shown in FIG. 8A. The other end of the implant member can be constructed to end with one of the loops illustrated in FIG. 8A. That loop is then sutured to the tissue with conventional suture techniques. Alternatively, it can be secured to the tissue using a surgical clip such as any one of the clips described above.

In yet a further case, both clip anchors and their release mechanisms and delivery needles can be eliminated and both ends of the implant member constructed to end in a loop as described above. Both loops can then be fastened to the tissue using a suture or clip as described with respect to the previous example.

In another variation, the implant member can be a full ring and the loops secured to tissue thereunder.

Referring to FIG. 11, an alternative tissue connector assembly suitable for use with system 200 to secure the implant member ends and/or loops to the valve tissue is shown. The tissue connector assembly 400 generally comprises a needle 106, tubular flexible member 104, clip or anchor 204 (all of which have been described above) and a remote release mechanism "R." Although the squeeze actuated release mechanism 208 is very effective, a remote release mechanism is especially advantageous where the operative space or field is limited such as in the case of valve annuloplasty. Various remote release mechanisms in accordance with the disclosure are illustrated in FIGS. 12A-12D, 13A-13D, and 14A-14D. Generally, the remote release mechanism "R" comprises a holding mechanism, such as the plurality of arms or wires 122 illustrated in FIGS. 2A-D, and a sheath or tubular member for holding the holding mechanism closed, such as tubular member 124 illustrated in FIGS. 2A-D and, therefore can be the same as release mechanism 108.

More specifically, when constructed for holding a clip or anchor, the holding mechanism or member(s) can comprise multiple strands, cables or wires 122 having a radially outward bias as shown in FIGS. 12A-12D, two halves 122' of hypodermic tubing as shown in FIGS. 13A-13D (with recesses 126' for receiving the surgical clip and having an inner diameter less than the diameter of enlarged portion E1), or one piece of hypodermic tubing 122" as shown in FIGS. 14A-14D. That is the holding mechanism has recesses 126, 126', or 126" formed therein to receive and/or hold the enlarged end E1 of the clip or anchor 204. Clip anchor 204 also has an enlarged end E2 as shown in FIG. 11. In the embodiment of FIGS. 12A-D, the strands 122 have notches 128, as shown in FIGS. 2A-D, to hold enlarged portion 134 of wire 136. Sleeve 124 is retracted to release the holding mechanism and the clip or anchor 204 as shown in FIGS. 12D, 13D, and 14D. The longer the sleeve, the more remotely one can actuate release of the clip.

The hypodermic halves shown in FIGS. 13A-D, also have cut out portions that form arms 240 and collars 242. Collars 242 surround wire 136 and have inner diameters less than the diameter of enlarged portion or ball 134 to secure halves 122' to wire 136. In this manner, the delivery apparatus can be readily removed, while leaving the clip or anchor at the desired site.

The one-piece hypodermic tubing embodiment of FIGS. 14A-D, has a cut out to form a longitudinal opening for releasing a clip or anchor 204 from holding member 122". The tubing also has cut outs to form arm 240' and collar 242' having an inner diameter less than the diameter of enlarged portion or ball 134 to secure the tubing to wire 136 and facilitate removal of the delivery apparatus, while leaving the clip or anchor at the desired site.

While the disclosure has been described with reference to specific embodiments, the disclosure by no means is limited to the specific embodiments illustrated and described herein. It is recognized that departures from the disclosed embodiments may be made within the scope of the disclosure and that obvious modifications will occur to a person skilled in the art. Accordingly, all suitable modifications and equivalents may be resorted to the extent that they fall within the scope of the disclosure and claims appended hereto.

What is claimed is:

1. An annuloplasty system for repairing a valve in a patient's heart, the annuloplasty system comprising:
    an implant member having a longitudinal length defined between opposing, first and second end portions, where the implant member naturally self-reverts to a crescent shape along the longitudinal length, the implant member having a plurality of curves pre-formed therein and being adapted to form a partial ring along a portion of an annulus of a valve in a patient's heart, wherein the curves are interconnected to collectively apply a recoil force onto the first and second end portions to draw the first and second end portions of the implant member toward one another in an axial direction;
    a first anchor connected to the first end portion;
    a first flexible member;
    a first release mechanism attached to a first end of the flexible member and releasably connected with one of the first end portion and the first anchor, the first release mechanism including a holding mechanism defining an aperture sized to releasably capture a section of one of the first end portion and the first anchor such that in a first state of the holding mechanism, the flexible member is connected with the section, and in a second state of the holding mechanism, the flexible member is disconnected from the section; and
    a needle connected to an opposite, second end of the flexible member.

2. The annuloplasty system of claim 1, wherein the release mechanism further includes a sleeve slidably disposed over the holding mechanism.

3. The annuloplasty system of claim 2, wherein the holding mechanism includes a plurality of arms collectively defining the aperture.

4. The annuloplasty system of claim 3, wherein the sleeve is slidable relative to the plurality of arms between a first position in which the sleeve is over the aperture and a second position in which the sleeve is longitudinally displaced from the aperture.

5. The annuloplasty system of claim 1, wherein the implant member is a wire.

6. The annuloplasty system of claim 5, wherein the wire forms the plurality of curves as a series of undulations.

7. The annuloplasty system of claim 5, wherein the wire forms the plurality of curves as a series of closed loops.

8. The annuloplasty system of claim 5, wherein the plurality of curves are formed along an intermediate segment of the wire.

9. The annuloplasty system of claim 8, wherein the first end portion is free of the plurality of curves.

10. The annuloplasty system of claim 8, wherein the first end portion extends from the intermediate segment and terminates at a first end, and further wherein the first anchor is disposed over the first end portion between the first end and the intermediate segment.

11. The annuloplasty system of claim 10, wherein the first anchor includes a wound coil, and further wherein the wound coil and the first end portion combine to form a self-closing clip.

12. The annuloplasty system of claim 5, wherein the anchor is a self-closing clip attached to a terminal end of the first end portion.

13. The annuloplasty system of claim 5, wherein the wire has a diameter, and further wherein the anchor is transitionable from a delivery state to a deployed state, an outer diameter of the anchor in the deployed state being greater than a diameter in the delivery state, and of the diameter of the wire.

14. The annuloplasty system of claim 1, further comprising:
a second anchor connected to the second end portion;
a second flexible member releasably connected to one of the second anchor and the second end portion; and
a second needle attached to the second flexible member.

15. The annuloplasty system of claim 14, further comprising a second release mechanism releasably connecting the second flexible member with one of the second end portion and the second anchor.

16. The annuloplasty system of claim 14, further comprising a plurality of self-closing clips apart from the first and second anchors for securing portions of the implant member to tissue.

* * * * *